US009498737B2

(12) United States Patent
Nakamura et al.

(10) Patent No.: US 9,498,737 B2
(45) Date of Patent: Nov. 22, 2016

(54) METHOD OF PURIFYING NUCLEIC ACIDS, METHOD OF EXTRACTING NUCLEIC ACIDS AND KIT FOR PURIFYING NUCLEIC ACIDS

(75) Inventors: Tomohiko Nakamura, Tokyo (JP); Naohisa Sakamoto, Tokyo (JP);
(Continued)

(73) Assignee: Sony Corporation, Tokyo (JP)

( * ) Notice: Subject to any disclaimer, the term of this patent is extended or adjusted under 35 U.S.C. 154(b) by 172 days.

(21) Appl. No.: 14/239,340

(22) PCT Filed: Aug. 28, 2012

(86) PCT No.: PCT/JP2012/005384
§ 371 (c)(1),
(2), (4) Date: Feb. 18, 2014

(87) PCT Pub. No.: WO2013/038604
PCT Pub. Date: Mar. 21, 2013

(65) Prior Publication Data
US 2014/0197107 A1 Jul. 17, 2014

(30) Foreign Application Priority Data
Sep. 13, 2011 (JP) ................. 2011-198949

(51) Int. Cl.
*B01D 15/36* (2006.01)
*B01J 39/04* (2006.01)
(Continued)

(52) U.S. Cl.
CPC ........... *B01D 15/362* (2013.01); *B01D 15/363* (2013.01); *B01J 39/04* (2013.01); *B01J 41/04* (2013.01);
(Continued)

(58) Field of Classification Search
USPC ....................................................... 210/663
See application file for complete search history.

(56) References Cited

U.S. PATENT DOCUMENTS

2002/0042506 A1* 4/2002 Kristyanne .......... C12N 15/101
536/25.4
2004/0016702 A1* 1/2004 Hennessy ............ B01J 20/3293
210/660
(Continued)

FOREIGN PATENT DOCUMENTS

EP   1 674 570 A2   6/2006
EP   1 715 039 A1   10/2006
(Continued)

OTHER PUBLICATIONS

Extended European Communication Pursuant to Rule 64 EPC Supplementary European Search Report issue Jul. 24, 2015 for corresponding European Application No. 12832581.8.
(Continued)

*Primary Examiner* — Chester Barry
(74) *Attorney, Agent, or Firm* — Michael Best & Friedrich LLP

(57) ABSTRACT

[Object] To provide a method of purifying nucleic acids where the operation is simple and the nucleic acids can be extracted in a short time with high efficiency.
[Solving Means] A method of purifying nucleic acids including the step of adsorbing substances in a sample containing nucleic acids with an ion exchange resin 10 including a positive ion exchange resin and a negative ion exchange resin. As the positive ion exchange resin, a first positive ion exchange resin and a second positive ion exchange resin having an exclusion limit molecular weight lower than that of the first positive ion exchange resin may be used.

20 Claims, 8 Drawing Sheets

(75) Inventors: Tasuku Yotoriyama, Tokyo (JP);
Kazumine Ito, Tokyo (JP)

(51) Int. Cl.
*B01J 41/04* (2006.01)
*C12Q 1/68* (2006.01)
*C12N 15/09* (2006.01)
*G01N 30/88* (2006.01)
*C12N 15/10* (2006.01)
*G01N 30/96* (2006.01)

(52) U.S. Cl.
CPC ............. *C12N 15/09* (2013.01); *C12N 15/101* (2013.01); *C12Q 1/68* (2013.01); *C12Q 1/6806* (2013.01); *G01N 30/88* (2013.01); *G01N 30/96* (2013.01); *G01N 2030/8827* (2013.01)

(56) References Cited

U.S. PATENT DOCUMENTS

| | | | |
|---|---|---|---|
| 2005/0130196 A1 | 6/2005 | Hofstadler et al. | |
| 2008/0076912 A1* | 3/2008 | Takkellapati | C12N 15/101 536/25.4 |
| 2012/0009560 A1* | 1/2012 | Coupe | C12Q 1/04 435/5 |

FOREIGN PATENT DOCUMENTS

| | | |
|---|---|---|
| JP | 2005-080555 A | 3/2005 |
| JP | 2007-516425 A | 6/2007 |
| WO | WO-00/69872 A2 | 11/2000 |
| WO | WO-00/70041 A1 | 11/2000 |
| WO | WO-02/48164 A2 | 6/2002 |
| WO | WO-03/101494 A1 | 12/2003 |
| WO | WO-2004/055213 A1 | 7/2004 |
| WO | WO-2008/035991 A2 | 3/2008 |
| WO | WO-2009-060847 A1 | 5/2009 |
| WO | WO-2010/072834 A1 | 7/2010 |
| WO | WO-2011/081869 A2 | 7/2011 |

OTHER PUBLICATIONS

Japanese Office Action issued Sep. 15, 2015 for corresponding Japanese Application No. 2011-198949.
International Search Report; Application No. PCT/2012/005384; Filed: Aug. 28, 2012. Completion of International Search Report: Nov. 28, 2012. (Form PCT/ISA/210).
Ikegami, Tohru, et al., "Anion- and Cation-Exchange MicroHPLC Utilizing Poly (methacrylates)-coated Monolithic Silica Capillary Columns" The Japan Society for Analytical Chemistry, Analytical Sciences Jan. 2007, vol. 23, pp. 109 to 113.
Huber, Christian G., et al. "On-Line Cation Exchange for Suppression of Adduct Formation in Negative-ion Electrospray Mass Spectrometry of Nucleic Acid" Institute of Analytical Chemistry and Radiochemistry, Leopold-Franzens-University, Innsbruck, Austria, 1998, 70, 5288-5295.
European Patent Office Communication Pursuant to Rule 164(1) EPC, Partial Supplementary European Search Report for corresponding European Application No. 12832581.8, (2015).
Bitner R. et al., "Use of Magnesiltm Paramagnetic Particles for Plasmid Purification, PCR Cleanup, and Purification of Dideoxy and Big Dye DNA Sequencing Reactions" Proceeding of SPIE International Society for Optical Engineering, US, vol. No. 3926, Jan. 1, 2000, pp. 126-133, XP000938886, ISSN: 0277-786X, DOI: 10.1117/12.380504.
Brown, D.M., et al. "Anion-cation Separations on a Mixed Bed Alumina-silica Column" Journal of Chromatography, Elsevier Science Publishers B.V. NL, vol. No. 466. Jan. 1, 1989, pp. 291-300, XP026479501, ISSN: 0021-9673. DOI: 10.1016/S0021-9673 (01) 84624-0.

* cited by examiner

METHOD OF PURIFYING NUCLEIC ACIDS, METHOD OF EXTRACTING NUCLEIC ACIDS AND KIT FOR PURIFYING NUCLEIC ACIDS

TECHNICAL FIELD

The present technology relates to a method of purifying nucleic acids, a method of extracting nucleic acids and a kit for purifying nucleic acids, and more particularly to a method of purifying nucleic acids by adsorbing foreign substances with an ion exchange resin.

BACKGROUND ART

A nuclear acid amplification reaction such as PCR (Polymerase Chain Reaction) and LAMP (Loop-Mediated Isothermal Amplification) is applied to a variety of fields in biotechnology. For example, in a medical field, a diagnosis is carried out based on base sequences of DNAs and RNAs. In an agriculture field, a DNA analysis is utilized to detect gene recombinant plants.

The nuclear acid amplification reaction can efficiently amplify and detect the nucleic acids in a minor amount of sample. However, if an extremely minor amount of the nucleic acids is included in the sample, the amount of the nucleic acids may be under the lower detection limit. Furthermore, a concentration of the nucleic acids in the sample is extremely low, the nucleic acids may not be detected because the nucleic acids to be amplified are not contained in the sample having a volume that can be fed into a reaction site. In these cases, it is effective to feed the nucleic acids that are extracted by purifying, concentrating etc. in advance to a reaction site.

Here, by focusing on purifying the nucleic acids, a conventional method using phenol/chloroform/ethanol is known. Also, a method of purifying the nucleic acids using a porous carrier having a nucleic acid adsorbing ability is known (See Patent Document 1).

Patent Document 1: Japanese Patent Application Laid-open No. 2005-080555
Patent Document 2: PCT Application Laid-open No. 2009/060847

SUMMARY OF INVENTION

Problem to be Solved by the Invention

However, in the conventional method using phenol/chloroform/ethanol, the use of toxic organic solvents is necessary and a centrifugation operation is an extra work. In the method of purifying the nucleic acids using a porous carrier having a nucleic acid adsorbing ability, a plurality of steps are necessary and a simple operation is unfeasible. Accordingly, there is strong needed a simple method of purifying nucleic acids in a short time with high efficiency.

A main object of the present technology is to provide a simple method of purifying nucleic acids in a short time efficiently.

Means for Solving the Problem

In order to solve the above-described problem, the present technology provides a method of purifying nucleic acids including a step of adsorbing substances included in a sample containing the nucleic acids with an ion exchange resin; the ion exchange resin being a positive ion exchange resin and a negative ion exchange resin. The positive ion exchange resin allows cations of positively charged protein or a metal salt included in the sample to be adsorbed. The negative ion exchange resin allows negatively charged anions included in the sample other than the nucleic acids to be adsorbed.

As the positive ion exchange resin, a first positive ion exchange resin and a second positive ion exchange resin having an exclusion limit molecular weight lower than that of the first positive ion exchange resin are desirably used. Herein, the exclusion limit molecular weight refers to a lowest molecular weight of the compound to be adsorbed by the ion exchange resin that is difficult to enter pores of the ion exchange resin, i.e., is difficult to be adsorbed within the pores of the ion exchange resin. In other words, the compound having the molecular weight higher than the exclusion limit molecular weight is difficult to be adsorbed by the ion exchange resin.

Among the positive ion exchange resins, the first positive ion exchange resin having the higher exclusion limit molecular weight may be easy to selectively adsorb the protein. In addition, among the positive ion exchange resins, the second positive ion exchange resin having the lower exclusion limit molecular weight may be easy to selectively adsorb mainly the cation such as the metal salt.

It is desirable that after the substances be adsorbed by the first positive ion exchange resin, the substances be adsorbed by the negative ion exchange resin and the second ion exchange resin. In this case, a column includes the first positive ion exchange resin in an upper layer and the negative ion exchange resin and the second positive ion exchange resin in a lower layer. The sample may be flowed into the column from an upper layer side. In this way, as to the substances in the sample, the protein in the sample is selectively adsorbed mainly by the first positive ion exchange resin, and the metal salt in the sample is selectively adsorbed mainly by the second positive ion exchange resin and the negative ion exchange resin, thereby improving adsorption efficiency of the substances in the sample.

Also, the step may adsorb the substances included in the sample that is diluted with a buffer solution by the ion exchange resin. Desirably, the buffer solution has a pH of 4.0 to 8.0.

Desirably, the positive ion exchange resin is a strong acidic positive ion exchange resin. Desirably, counter ions of the first positive ion exchange resin are $Na^+$ (sodium ions). Desirably, the counter ions of the negative ion exchange resin are $OH^-$ (hydroxide ions).

Desirably, the negative ion exchange resin is a strong basic negative ion exchange resin. Desirably, counter ions of the negative ion exchange resin are $OH^-$ (hydroxide ions).

Also, desirably, a percentage of an ion exchange capacity of the negative ion exchange resin to the second positive ion exchange resin is 50% to 150%. Herein, the ion exchange capacity refers to a total number of exchange groups per unit amount of the ion exchange resin. For example, when the counter ions of the second positive ion exchange resin are $H^+$, the ion exchange capacity refers to the total number of $H^+$ included in 1 ml of the second positive ion exchange resin. When the percentage of the ion exchange capacity of the negative ion exchange resin to the second positive ion exchange resin is 50% to 150%, it is possible to more stably inhibit a variation in pH before and after the adsorption of the substances included in the sample by the ion exchange resin.

In the method of purifying the nucleic acids, it is more desirable that a nonionic surfactant and/or a nonionic hydrophilic polymer compound be added to the sample to adsorb the substances. By adding the nonionic surfactant and/or the nonionic hydrophilic polymer compound to the sample, it is possible to inhibit physical adsorption of the nucleic acids to the resin.

The above-described substances are foreign substances, for example. The foreign substances contain protein and a metal salt, for example. The foreign substances may contain substances such as a variety of peptides, sugers, salts and low molecular anions (for example, fumaric acid, phthalic acid, humic acid and fulvic acid) that are unnecessary for the analysis of the nucleic acids in the sample in addition to the protein and the metal salt.

In order to solve the above-described problem, the present technology provides a method of purifying nucleic acids including steps of: ultrasonically treating the sample including nucleic acids, adsorbing substances included in the sample with a positive ion exchange resin and a negative ion exchange resin, and concentrating the nucleic acids by blocking the nucleic acids migrated by electrophoresis.

The electrophoresis may be carried out on the nucleic acids into which an intercalator having an anionic functional group is inserted. Also, the electrophoresis may be carried out on the nucleic acids by mixing the sample, a compound having a functional group that is reacted with a carboxyl group of the substances included in the sample by dehydration condensation and a condensation agent of the dehydration condensation reaction.

Furthermore, the present technology provides a kit for purifying nucleic acids including a positive ion exchange resin, a negative ion resin and a nucleic acid purifying instrument internally holding the positive ion exchange resin and the negative ion exchange resin for distributing a sample including nucleic acids.

Effect of the Invention

According to the present technology, there is provided a simple method of purifying nucleic acids in a short time efficiently.

MODE(S) FOR CARRYING OUT THE INVENTION

Figure 1:
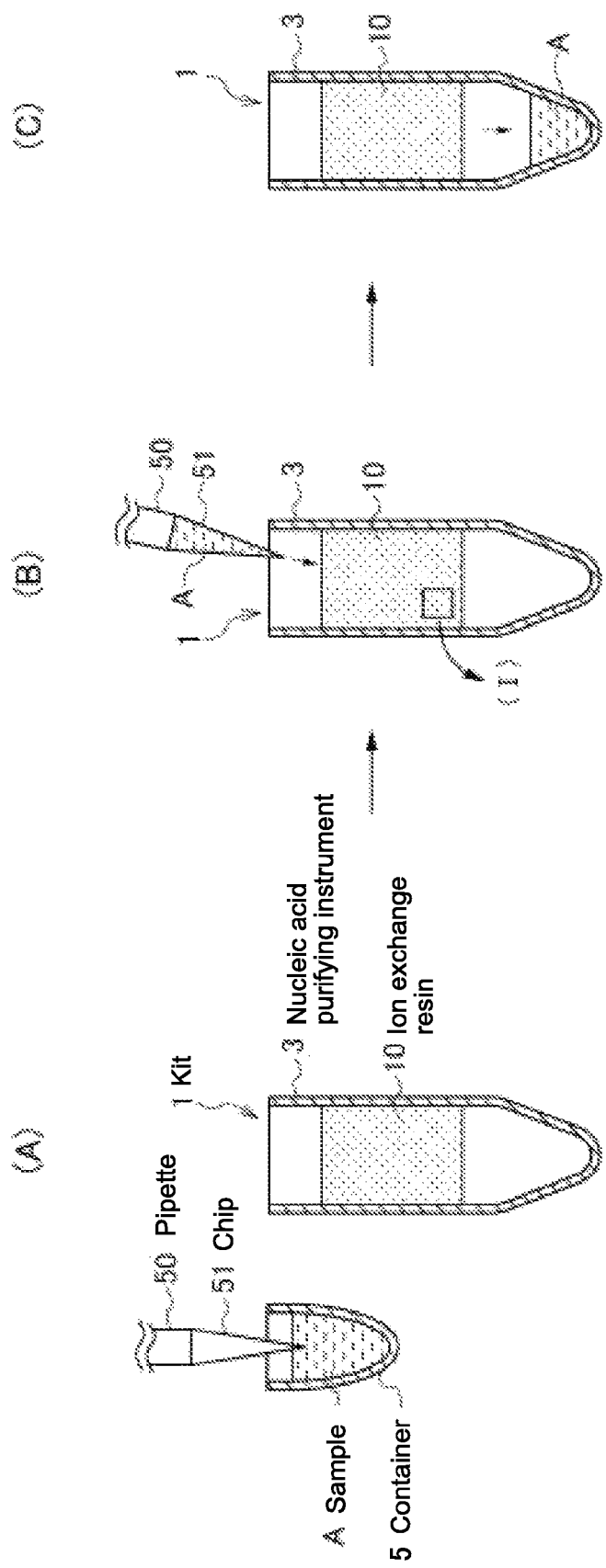
FIG. 1 A schematic view for illustrating steps of a method of purifying nucleic acids according to a first embodiment of the present technology.

Hereinafter, embodiments of the present disclosure will be described with reference to the drawings. The embodiments described below merely depict typical embodiments of the present disclosure, and the scope of the present disclosure should not be construed narrower. The embodiments will be described in the following order.
1. A kit for purifying nucleic acids and a method of purifying nucleic acids according to a first embodiment of the present technology
(1) A kit for purifying nucleic acids
(2) A method of purifying nucleic acids
2. A kit for purifying nucleic acids and a method of purifying nucleic acids according to a second embodiment of the present technology
3. A method of extracting nucleic acids
1. A Kit for Purifying Nucleic Acids and a Method of Purifying Nucleic Acids According to a First Embodiment of the Present Technology
(1) A Kit for Purifying Nucleic Acids Firstly, a kit for purifying nucleic acids used in a method of purifying nucleic acids according to a first embodiment of the present technology will be described referring to FIG. 1 (A). FIGS. 1 (A) to (C) are schematic views for illustrating steps of a method of purifying nucleic acids according to the first embodiment of the present technology.

In FIG. 1 (A), a kit 1 for purifying nucleic acids adsorb substances (hereinafter referred to as "foreign substances") included in the sample other than the nucleic acids, and purify the nucleic acids. The kit 1 for purifying nucleic acids mainly includes an ion exchange resin 10 and a nucleic acid purifying instrument 3 holding the ion exchange resin 10 inside and being capable of distributing the sample containing the nucleic acids. The sample used in the present technology is not especially limited, and may be a biological sample such as a swab, an oral cavity swab, saliva, blood sera, blood plasma, peripheral blood monocytes, cerebrospinal fluids, feces, urine, cultured cells and biopsy tissues, for example. In addition to the biological sample, the sample may also be river water, sea water, soil or the like.

The nucleic acid purifying instrument 3 holds the ion exchange resin 10 inside and distribute the sample. A shape, a material or the like of the nucleic acid purifying instrument 3 is not especially limited as long as the nucleic acid purifying instrument 3 can hold the ion exchange resin 10 inside and distribute the sample. For example, a commercially available sample tube, a chip or the like having an opening at an upper section as shown in FIG. 1 (A). Alternatively, the nucleic acid purifying instrument 3 may have a tube having opening at upper and lower sections. In this case, after the sample is distributed through the nucleic acid purifying instrument 3 and the sample is adsorbed by the ion exchange resin 10, a separate chip or the like can be used to recover the sample flowed from the lower section.

The ion exchange resin 10 according to the present technology adsorbs the foreign substances included in the sample. The ion exchange resin 10 includes a positive ion exchange resin and a negative ion exchange resin. For example, the foreign substances contain protein and a metal salt. The foreign substances may contain a variety of peptides, sugers, salts, low molecular anions (for example, fumaric acid, phthalic acid, humic acid and fulvic acid) that are unnecessary for the analysis of the nucleic acids in the sample in addition to the protein and the metal salt.

The above-described positive ion exchange resin mainly adsorbs cationic foreign substances. Desirably, the positive ion exchange resin includes a first positive ion exchange resin and a second positive ion exchange resin having an exclusion limit molecular weight lower than that of the first positive exchange resin. The first positive ion exchange resin is used to mainly adsorb the protein included in the sample. The second positive ion exchange resin is used to mainly adsorb the positive ions (cations) such as metal ions included in the sample.

Non-limiting example of the first positive ion exchange resin can be used as long as the protein included in the sample. Desirably, the first positive ion exchange resin is a strong acidic positive ion exchange resin. A fixed ion of the first positive ion exchange resin is desirably $SO_3^-$. Non-limiting examples of the counter ions include a calcium ion ($Ca^{2+}$), a copper ion ($Cu^{2+}$), a zinc ion ($Zn^{2+}$), a magnesium ion ($Mg^{2+}$), a potassium ion ($K^+$), an ammonium ion ($NH_4^+$), a sodium ion ($Na^+$), a proton ($H^+$) and the like. In this regard, ion exchange strength (ion selectivity) of these ions is in the order of $Ca^{2+}>Cu^{2+}>Zn^{2+}>Mg^{2+}>K^+>NH_4^+>Na^+>H^+$. Accordingly, in view of the ion exchange strength, the counter ions are desirably $H^+$. On the other hand, when the counter ions are $H^+$, a pH of the sample is likely to shift to an acidic side. In contrast, when the counter ions are $Na^+$, a function to adsorb the metal salt becomes lower than that when the counter ions are $H^+$. However, it is possible to inhibit the variation in the pH of the sample. Even if the counter ions are $Na^+$, the first positive ion exchange resin can fully adsorb protein. Therefore, the first positive ion exchange resin is desirably a strong acidic positive ion exchange resin (a $Na^+$ type strong acidic positive ion exchange resin) having $Na^+$ as the counter ions.

The second positive ion exchange resin is not especially limited as long as the cations such as the metal salt included in the sample can be adsorbed, but is desirably a strong acidic positive ion exchange resin. A fixed ion of the second positive ion exchange resin is desirably $SO_3^-$. The counter ions are not especially limited. However, in view of the order of the above-described ion exchange strength (ion selectivity), the counter ions of the second positive ion exchange rein are desirably protons ($H^+$).

The negative ion exchange resin adsorbs the positive ions (anions) included in the sample. Non-limiting example of the negative ion exchange resin can be used as long as the anions such as the metal salt included in the sample. Desirably, the negative ion exchange resin is a strong basic negative ion exchange resin. The negative ion exchange resin may be either of a I type strong basic negative ion exchange resin having a trimethyl ammonium group or a II type strong basic negative ion exchange resin having a dimethyl ethanol ammonium group. In the I type, the negative ion exchange strength (ion selectivity) of these ions is in the order of $HSO_4^->NO_3^->Br^->Cl^->HCO_3^->HCOO^->CH_3COO^->F^->OH^-$. In the II type, the negative ion exchange strength (ion selectivity) of these ions is in the order of $HSO_4^->NO_3^->Br^->Cl^->HCO_3^->OH^->HCOO^->CH_3^-COO^->F^-$. Among the I type and II type strong basic negative ion exchange resins, the I type strong basic negative ion exchange resin can adsorb chloride ions ($Cl^-$) and the like with higher accuracy. Thus, the negative ion exchange resin is desirably the I type and includes hydroxide ions ($OH^-$) as the counter ions.

The kit 1 for purifying nucleic acids may include an additive such as a non-ionic compound including a non-ionic surfactant, a non-ionic hydrophilic polymer compound or the like so that the nucleic acids are not adsorbed together with the foreign substances. Examples of the non-ionic compound include the non-ionic surfactant such as Brij35, Tween20 and TritonX100. Also, examples of the non-ionic hydrophilic polymer compound include polyethylene glycol, polyhydroxy ethyl cellulose or the like. These illustrated non-ionic compounds may be used alone or in combination. Furthermore, the kit 1 for purifying nucleic acids may contain a chelate additive such as EDTA.

The kit 1 for purifying nucleic acids may contain a buffer solution. Examples of a buffer agent for the buffer solution include HomoPIPES (pH: 3.9-5.1, pKa: 4.55), MES (pH: 5.5-7.0, pKa: 6.15), Bis-Tris (pH: 5.7-7.3, pKa: 6.46), ADA (pH: 5.8-7.4, pKa: 6.60), PIPES (pH: 6.1-7.5, pKa: 6.80), ACES (pH: 6.0-7.5, pKa: 6.90), MOPSO (pH: 6.2-7.4, pKa: 6.95), BES (pH: 6.6-8.0, pKa: 7.15), MOPS (pH: 6.5-7.9, pKa: 7.20), TES (pH: 6.8-8.2, pKa: 7.50), HEPES (pH: 6.8-8.2, pKa: 7.55), DIPSO (pH: 6.9-8.1, pKa: 7.6), TAPSO (pH: 7.0-8.2, pKa: 7.7), POPSO (pH: 7.2-8.5, pKa: 7.85), HEPPSO (pH: 7.4-8.6, pKa: 7.9), EPPS (pH: 7.5-8.5, pKa: 8.0), Tricine (pH: 7.8-8.8, pKa: 8.15), Bicine (pH: 7.7-9.1, pKa: 8.35), TAPS (pH: 7.7-9.1, pKa: 8.4), CHES (pH: 8.6-10.0, pKa: 9.5), CAPSO (pH: 9.3-10.7, pKa: 10.0), CAPS (pH: 9.7-11.1, pKa: 10.40) or the like. The pH range of each buffer agent cited above refers to an appropriate pH range of the sample to which the buffer agent is added. The pKa of each buffer agent cited above refers to a pKa at 20° C. excluding HomoPIPES (as to HomoPIPES, the pKa is at 37° C.). The pH of the buffer solution to which the sample is diluted is desirably 4 to 8. In this regard, HomoPIPES, MES, Bis-Tris and ADA are desirably used in the first embodiment among the buffer agents cited above.

(2) Method of Purifying Nucleic Acids

Next, steps of a method of purifying nucleic acids according to a first embodiment of the present technology will be described referring to FIGS. 1 (A) to (C).

Before describing the method of purifying nucleic acids according to the first embodiment of the present technology, a method of purifying nucleic acids in the related art of the present technology will be described. In the method of purifying nucleic acids in the related art, foreign substances in the sample are adsorbed using zeolite (see Patent Document 2, for example).

By the method of purifying nucleic acids in the related art, only cations among anions and cations included in the sample such as the biological sample can be removed. Thus, in the method of purifying nucleic acids in the related art, when the sample is purified, protons will be discharged, thereby decreasing the pH of the solution containing the sample (more shifting to the acidic side). In this regard, after the sample is purified, the nucleic acid amplification reaction may be carried out at the pH of 7 to 9. It is necessary to set the pH of the solution containing the sample being contacted with zeolite higher in advance (to set it at an alkali side). In this way, the method of purifying nucleic acids in the related art may be a cumbersome operation. Also, when the sample includes RNAs, the RNAs may be decomposed.

In the method of purifying nucleic acids in the related art, after the sample is diluted with a mixed reagent of an alkaline compound and a surfactant (for example, SDS), the sample is heated at high temperature. Also in this regard, the method of purifying nucleic acids in the related art may be a cumbersome operation. Also, when the sample includes RNAs, the RNAs may be decomposed.

In addition, in the method of purifying nucleic acids in the related art, after the sample is purified, anions may remain in the sample. Further, an anionic surfactant may be included in the sample. Thus, when the nucleic acids are electrophoresed after purification of the sample, the sample may have a high electrolyte concentration and easily generate heat. Also in this regard, when the sample includes RNAs, the RNAs may be decomposed. In addition, a convention flow of the sample is induced by the heat generation, thereby decreasing efficiency of electrophoresis condensation of the nucleic acids.

In contrast, the method of purifying nucleic acids according to the present technology described below in detail has been found by the present inventors through their intensive studies, needs no cumbersome operation, very simplifies the operation, and is a simple method capable of purifying nucleic acids in a short time with high efficiency.

In the method of purifying nucleic acids according to the first embodiment of the present technology, a sample A containing nucleic acids housed in a container 5 and a buffer solution for diluting the sample A are filled into a pipette tip 51 attached to a pipette 50 (see FIG. 1 (A)). Next, the sample A and the buffer solution for diluting the sample A filled into the pipette 50 are injected into a nucleic acid purifying instrument 3 (see FIG. 1 (B)). At this time, as the nucleic acid purifying instrument 3 holds the ion exchange resin 10 inside, the foreign substances included in the sample A are adsorbed by the ion exchange resin 10.

Finally, the sample A purified by adsorbing the foreign substances with the ion exchange resin 10 passes through the ion exchange resin 10 and is pooled at a bottom of the nucleic acid purifying instrument 3 (see FIG. 1 (C)).

After the steps shown in FIGS. 1 (A) to (C), the nuclear acid amplification reaction can be carried out on the sample A. For example, the nuclear acid amplification reaction can be carried out by adding the sample A to a solidified nuclear acid amplification reagent. In the first embodiment, the sample may be demineralized by the ion exchange resin 10 to change double helical DNAs into single stranded DNAs. Thus, the DNAs may be modified as appropriate before the nuclear acid amplification reaction.

Figure 2:
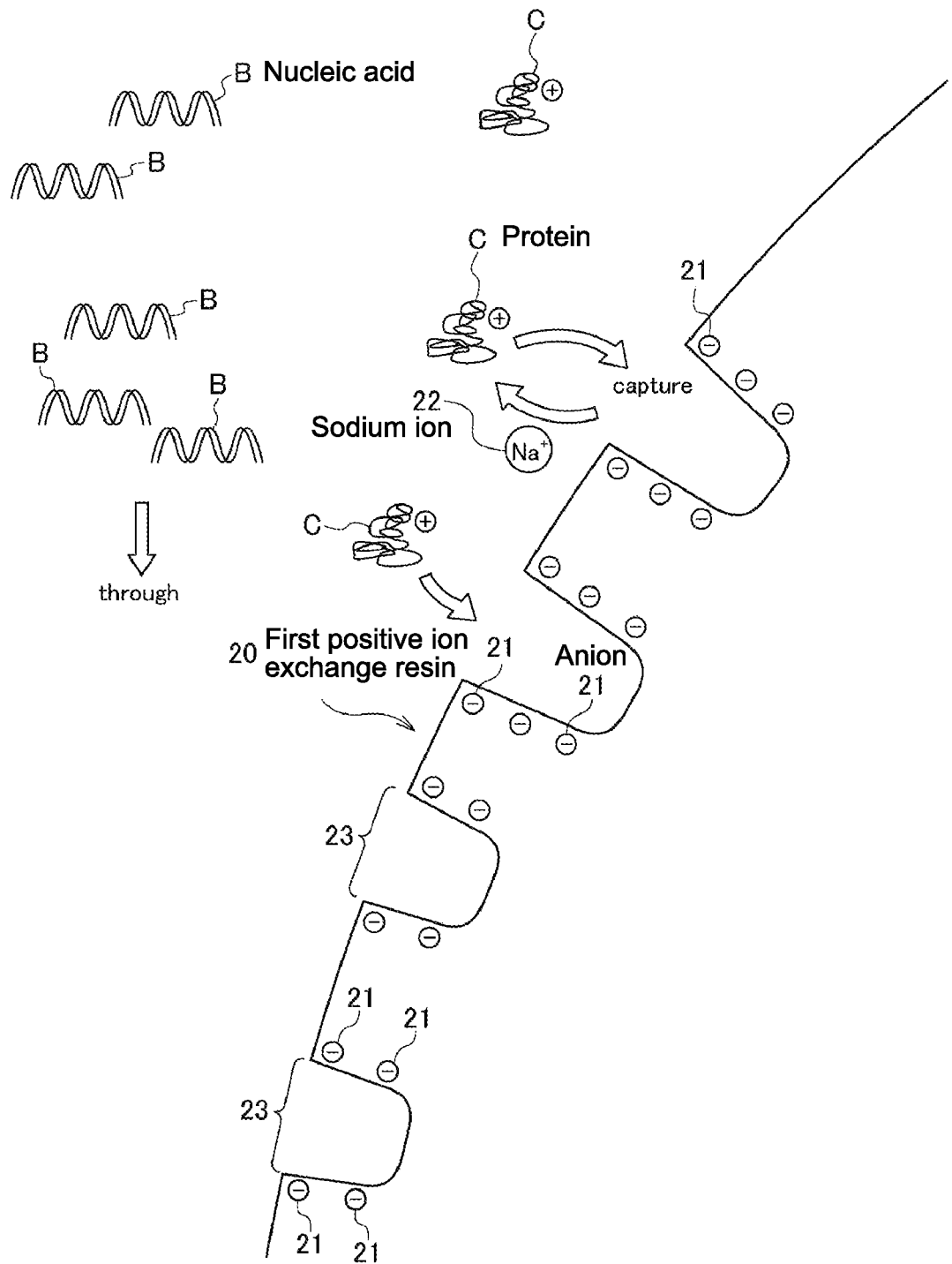
FIG. 2 A schematic view for conceptually illustrating a status that foreign substances are adsorbed by a first positive ion exchange resin according to a first embodiment of the present technology.
Figure 3:
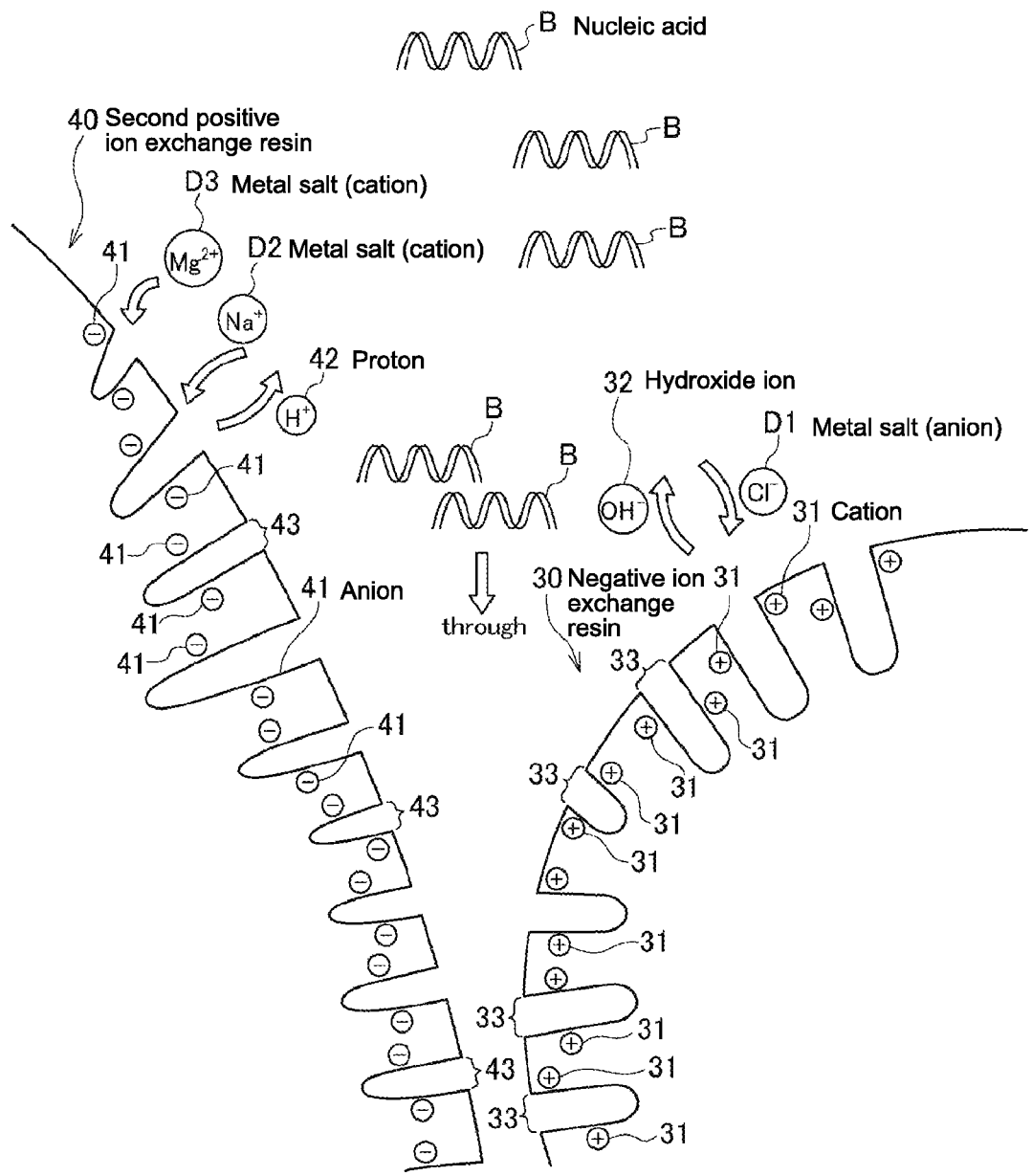
FIG. 3 A schematic view for conceptually illustrating a status that foreign substances are adsorbed by a second positive ion exchange resin and a negative ion exchange resin according to a first embodiment of the present technology.

Here, referring to FIGS. 2 and 3, a status that the foreign substances included in the sample A are adsorbed by the ion exchange resin 10 ((I) in FIG. 1 (B)) will be described in detail. FIG. 2 is a schematic view for conceptually illustrating the status that the foreign substances are adsorbed especially by the first positive ion exchange resin shown in FIG. 1 (B). FIG. 3 is a schematic view for conceptually illustrating the status that the foreign substances are adsorbed especially by the second positive ion exchange resin and the negative ion exchange resin shown in FIG. 1 (B).

Referring to FIG. 2, the status that the foreign substances included in the sample A are adsorbed by a first positive ion exchange resin 20 included in the ion exchange resin 10. In FIG. 2, nucleic acids B are included in the sample A and protein C is one of the foreign substances included in the sample A. Here, the first positive ion exchange resin 20 will be the strong acidic positive ion exchange resin having sodium ions ($Na^+$) as the counter ions.

The first positive ion exchange resin 20 includes anions 21 such as $SO_3^-$ and the counter ions $Na^+$ 22. In addition, areas 23 for adsorbing the protein C is formed on the first positive ion exchange resin 20.

As shown in FIG. 2, as the protein C included in the sample A flowed into the nucleic acid purifying instrument 3 is positively charged, the protein C is adsorbed by the first positive ion exchange resin 20 having the anions 21 on the surface. For example, the protein C is adsorbed at the areas 23. On the other hand, as the nucleic acids B are negatively charged, the nucleic acids B are not adsorbed by the first positive ion exchange resin 20, and are induced by and flows through the buffer solution or the like included in the sample A. In addition, as the counter ions of the first positive exchange resin 20 are $Na^+$ 22, the first positive exchange resin 20 less adsorb (demineralize) the metal salt but can selectively adsorb the protein C, as compared with the case where the counter ions are $H^+$.

In this case, the buffer solution for diluting the sample A has desirably the pH of 4 to 8. With the buffer solution for diluting the sample A having the pH of 4 to 8 (acidic), only the foreign substances (mainly, the protein C) can be positively charged while the nucleic acids B are negatively charged. In this way, only the protein C can be stably adsorbed by the ion exchange resin 20 and the nucleic acids B can be purified with high efficiency. In addition, as the first positive ion exchange resin 20 is the strong acidic positive ion exchange resin, the first positive ion exchange resin 20 can be negatively charged under a wide range of the pH conditions (for example, pH of 3 to 13). As described above, even if the sample is acidic, the first positive ion exchange resin 20 can stably adsorb the protein C. Furthermore, with the sample A having the pH of 4 to 8 (acidic), activity of RNases can be suppressed, thereby favorably purifying the RNA.

The exclusion limit molecular weight of the first positive ion exchange resin 20 is desirably such that the protein C included in the sample A is brought into the areas 23. More specifically, the exclusion limit molecular weight of the first positive ion exchange resin 20 is desirably 5000 or more. When the exclusion limit molecular weight of the first positive ion exchange resin 20 is 5000 or more, the protein C is easily and particularly selectively adsorbed and removed from the foreign substances.

A mean volume particle diameter of the first positive ion exchange resin 20 is desirably 1 μm to 3000 μm. When the mean volume particle diameter of the first positive ion exchange resin 20 is 1 μm to 3000 μm, the protein C is easily and particularly selectively adsorbed and removed from the foreign substances.

A specific gravity of particles themselves in the first positive ion exchange resin 20 is desirably 0.5 to 2.5. When the specific gravity of the first positive ion exchange resin 20 is 0.5 to 2.5, the protein C is easily and particularly selectively adsorbed and removed from the foreign substances. More desirably, the specific gravity of the particles themselves is 1.0 to 2.5. When the specific gravity is 1.0 to 2.5, the particles are easily settled within the solution, whereby it is possible to easily remove the particles from the solution.

Next, FIG. 3 illustrates the status that the foreign substances included in the sample A are adsorbed by a negative ion exchange resin 30 and a second positive ion exchange resin 40 included in the ion exchange resin 10.

In FIG. 3, each designated symbol D1, D2 or D3 is the cation or the anion included in the metal salt that is an example of the foreign substances included in the sample A. Although it is not especially limited in the first embodiment, D1 denotes the anion such as a chloride ion, D2 denotes the cation such as a sodium ion, and D3 denotes the cation such as a magnesium ion.

Referring to FIG. 3, the status that the negative ion exchange resin 30 adsorbs the foreign substances (mainly the anions such as the chloride ion) will be described. In the first embodiment, the negative ion exchange resin 30 is the I type strong basic negative ion exchange resin having hydroxide ions (OH$^-$) as the counter ions.

The negative ion exchange resin 30 has cations 31 such as $CH_2N(CH_3)_3^+$ and the counter ions such as OH$^-$ 32. In addition, areas 33 for adsorbing the anions such as the chloride ion D1 are formed in the negative ion exchange resin 30.

As shown in FIG. 3, the chloride ion D1 included in the sample A flowed into the nucleic acid purifying instrument 3 is negatively charged, and is adsorbed by the negative ion exchange resin 30 having the cations 31 on the surface. For example, the chloride ion D1 is adsorbed onto the areas 33. Although the nucleic acid B is also negatively charged, the nucleic acid B has a volume larger than the anion such as the chloride ion D1 and is therefore less adsorbed by the negative ion exchange resin 30. In this regard, the exclusion limit molecular weight of the negative ion exchange resin 30 is desirably 100 to 2000. When the exclusion limit molecular weight of the negative ion exchange resin 30 is 100 to 2000, the adsorption of the nucleic acid B is inhibited with higher accuracy and the cations such as the chloride ion D1 are selectively adsorbed and easily removed.

A mean volume particle diameter of the negative ion exchange resin 30 is desirably 1 μm to 3000 μm. When the mean volume particle diameter of the first positive ion exchange resin 20 is 1 μm to 3000 μm, the cations such as the chloride ion D1 are selectively adsorbed and easily removed.

A specific gravity of the negative ion exchange resin 30 is desirably 0.5 to 2.5. When the specific gravity of the negative ion exchange resin 30 is 0.5 to 2.5, the cations such as the chloride ion D1 are selectively adsorbed and easily removed with higher accuracy. More desirably, the specific gravity of the particles themselves is 1.0 to 2.5. When the specific gravity is 1.0 to 2.5, the particles are easily settled within the solution, whereby it is possible to easily remove the particles from the solution.

Next, FIG. 3 illustrates the status that the foreign substances (mainly the cations of the sodium ion D2 and the magnesium ion D3) are adsorbed by the second positive ion exchange resin 40. In the first embodiment, the second positive ion exchange rein 40 is the strong acidic positive ion exchange resin having H$^+$ ions (protons) as the counter ions.

The second positive ion exchange rein 40 has anions 41 such as $SO_3^-$ and H$^+$ 42. In addition, areas 43 for adsorbing the cations such as the sodium ion D2 and the magnesium ion D3 are formed in the second positive ion exchange resin 40.

As shown in FIG. 3, the sodium ion D2 and the magnesium ion D3 included in the sample A flowed into the nucleic acid purifying instrument 3 are positively charged, and are adsorbed by the second positive ion exchange resin 40 having the anions 41 on the surface. For example, the sodium ion D2 and the magnesium ion D3 are adsorbed onto the areas 43. On the other hand, the nucleic acids B are negatively charged, are therefore not adsorbed by the second positive ion exchange resin 40, and are induced by and flow through the buffer solution included in the sample A.

Here, the second positive ion exchange resin 40 has the exclusion limit molecular weight lower than that of the first positive ion exchange resin 20. Accordingly, the second positive ion exchange resin 40 has an increased surface area per unit area, and is easily demineralized as compared to the first positive ion exchange resin 20. When the second positive ion exchange resin 40 has protons as the counter ions, the second positive ion exchange resin 40 is easily demineralized as compared to the first positive ion exchange resin 20. The exclusion limit molecular weight of the second positive ion exchange resin 40 is desirably 100 to 2000. When the exclusion limit molecular weight of the second positive ion exchange resin 40 is 100 to 2000, the adsorption of the cations such as the sodium ion D2 and the magnesium ion D3 can be adsorbed with higher accuracy.

A mean volume particle diameter of the second positive ion exchange resin 40 is desirably 1 μm to 3000 μm. When the mean volume particle diameter of the second positive ion exchange resin 40 is 1 μm to 3000 μm, the cations such as the sodium ion D2 and the magnesium ion D3 can be adsorbed with higher accuracy. The mean volume particle diameter of the second positive ion exchange resin 40 is more desirably 1 μm to 2000 μm. When the mean volume particle diameter of the second positive ion exchange resin 40 is 1 μm to 2000 μm, it is possible to decrease a pressure when the solution flows through the ion exchange resin.

A specific gravity of the second positive ion exchange resin 40 is desirably 0.5 to 2.5. When the specific gravity of the second positive ion exchange resin 40 is 0.5 to 2.5, the cations such as the sodium ion D2 and the magnesium ion D3 can be adsorbed with higher accuracy. More desirably, the specific gravity of the particles themselves is 1.0 to 2.5. When the specific gravity is 1.0 to 2.5, the particles are easily settled within the solution, whereby it is possible to easily remove the particles from the solution.

Also, desirably, the percentage of the ion exchange capacity of the negative ion exchange resin 30 to the second positive ion exchange resin 40 is 50% to 150%. When the percentage of the ion exchange capacity is 50% to 150%, the sample can be demineralized while the variation in the pH is more stably inhibited.

Also, desirably, a percent amount of the negative ion exchange resin 30 to the second positive ion exchange resin 40 is 50% to 150%. When the percent amount is 50% to 150%, the sample can be demineralized while the variation in the pH is more stably inhibited.

Although not shown in FIGS. 2 and 3, the non-ionic surfactant such as Brij35, Tween20 and TritonX100 is added to the sample as appropriate in order to inhibit the nucleic acids B from adsorbing by the ion exchange resin. Also, the non-ionic hydrophilic polymer compound such as polyethylene glycol and polyhydroxy ethyl cellulose is desirably added to the sample A as appropriate.

According to the method of purifying nucleic acids of the first embodiment of the present technology as described above, the ion exchange resin 10 including the positive ion exchange resin and the negative ion exchange resin is used as an adsorbing carrier, thereby adsorbing the foreign substances included in the sample. For example, when the sample if a blood sample, the step of adsorbing can be directly carried out with no complex pretreatment steps. Thus, the method of purifying nucleic acids according to the first embodiment can extract the nucleic acids by a very simple operation in a short time with high efficiency. Specifically, only a few seconds is necessary to conduct all steps in the method of purifying nucleic acids. In this way, the nucleic acids can be purified in such a short time.

As the method of purifying nucleic acids according to the first embodiment includes no cleaning steps dissimilar to a silica solid-phase extraction, for example, only a minor amount of the sample is necessary for the operation and the apparatus can also be downsized. Also, the method of purifying nucleic acids according to the first embodiment can adsorb the foreign substances such that the sample is held under the acidic condition (desirably pH of 4 to 8). In other words, the method of purifying nucleic acids according to the first embodiment does not need the sample to be changed to alkali or heated. Accordingly, when the sample contains RNAs, the sample can be purified while the RNAs are inhibited from decomposing. In addition, in the method of purifying nucleic acids according to the first embodiment, when an ultrasonic disintegration is carried out at the acidic area, the function of RNase can be suppressed.

When the nuclear acid amplification reaction is carried out by using the solidified nuclear acid amplification reagent, the sample is not diluted and the foreign substances obviously inhibit the nuclear acid amplification reaction. However, as the sample purified by the method of purifying nucleic acids according to the first embodiment includes no foreign substances, the nuclear acid amplification reaction can be carried out by adding the nucleic acids directly to the solidified nuclear acid amplification reagent.

According to the method of purifying nucleic acids of the first embodiment of the present technology, the first positive ion exchange resin and the second positive ion exchange resin having the exclusion limit molecular weight lower than that of the first positive ion exchange resin can be used as the positive ion exchange resin. Accordingly, when the foreign substances in the sample contain the metal salt and the protein, both of them can be efficiently removed.

To adsorb and remove the foreign substances in the sample by the method of purifying nucleic acids according to the first embodiment, it is more effective that the first positive ion exchange resin and the second positive ion exchange resin each is the strong acidic positive ion exchange resin. The foreign substances are removed more efficiently when the counter ions of the first positive ion exchange resin are $Na^+$, or the counter ions of the second positive ion exchange resin are $H^+$.

In the method of purifying nucleic acids according to the first embodiment, the foreign substances are more efficiently removed when the negative ion exchange resin is the strong basic positive ion exchange resin. When the counter ions of the negative ion exchange resin are $OH^-$, the foreign substances are more efficiently removed.

According to the method of purifying nucleic acids according to the first embodiment, the percentage of the ion exchange capacity of the negative ion exchange resin to the second positive ion exchange resin is 50% to 150%, whereby the variation in the pH in the sample can be inhibited. As described above, when the sample contains RNAs, the sample can be purified while the RNAs are inhibited from decomposing.

In the method of purifying nucleic acids according to the first embodiment, the nonionic compound such as the nonionic surfactant and the non-ionic hydrophilic polymer compound can be used. In this case, the nucleic acids are inhibited from adsorbing to a matrix of the ion exchange resin and the foreign substances can be efficiently removed.

2. A Kit for Purifying Nucleic Acids and a Method of Purifying Nucleic Acids According to a Second Embodiment of the Present Technology FIGS. 4 (A) to (C) are schematic views for illustrating steps of a method of purifying nucleic acids according to the second embodiment of the present technology.

Figure 4:
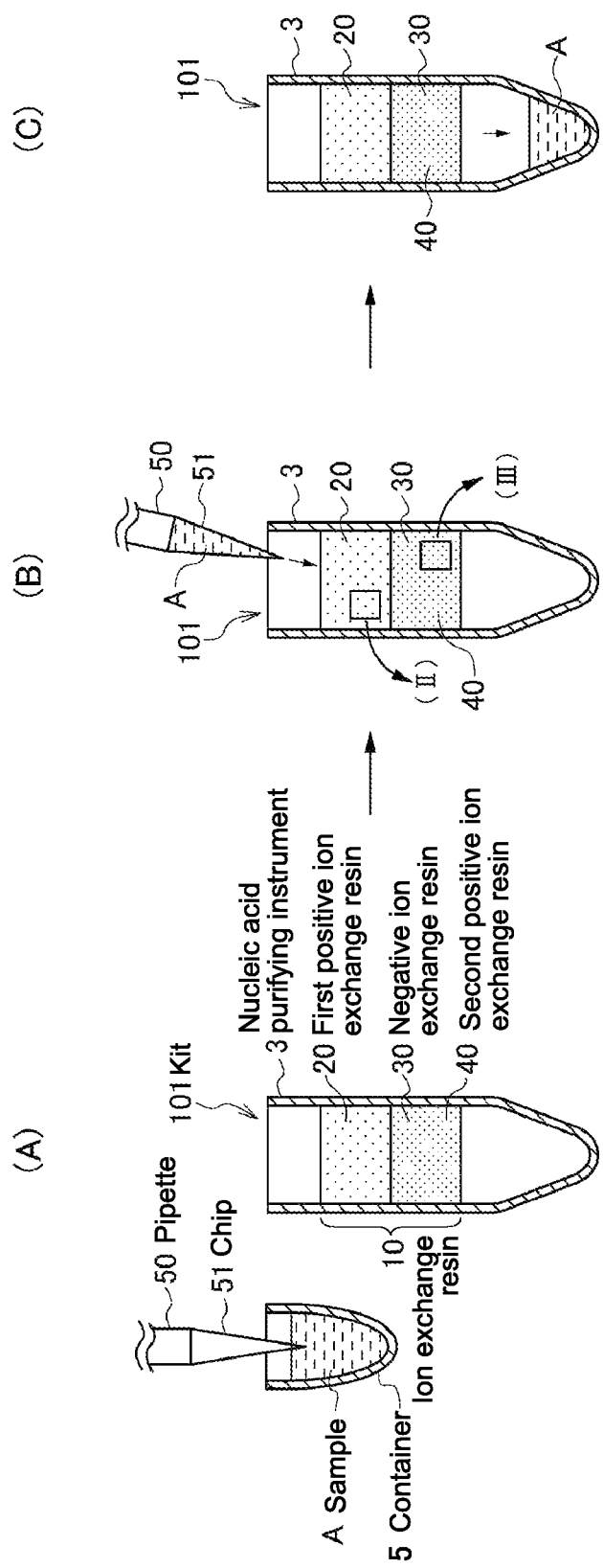
FIG. 4 A schematic view for illustrating steps of a method of purifying nucleic acids according to a second embodiment of the present technology.

In FIG. 4 (A), a kit 101 for purifying nucleic acids includes the ion exchange resin 10 and the nucleic acid purifying instrument 3 holding the ion exchange resin 10 inside and being capable of distributing the sample containing the nucleic acids. The ion exchange resin 10 includes the positive ion exchange resin and the negative ion exchange resin. In the kit 101 for purifying nucleic acids according to the second embodiment, the positive ion exchange resin includes the first positive ion exchange resin 20 and the second positive ion exchange resin 40.

The kit for purifying nucleic acids and the method of purifying nucleic acids according to the second embodiment is mainly different from the kit for purifying nucleic acids and the method of purifying nucleic acids according to the first embodiment in that the nucleic acids are purified while the first positive ion exchange resin 20 is housed in an upper layer (at a side where the sample is injected) of the negative ion exchange resin 30 and the second positive ion exchange resin 40. For this purpose, the position of the first positive ion exchange resin 20 disposed at the upper layer of the negative ion exchange resin 30 and the second positive ion exchange resin 40 will be mainly described in the second embodiment.

In the method of purifying nucleic acids according to the second embodiment, the first positive ion exchange resin 20 is housed in an upper layer side of the negative ion exchange resin 30 and the second positive ion exchange resin 40 within the nucleic acid purifying instrument 3. Thus, the sample A injected from the upper layer side is firstly contacted with the first positive ion exchange resin 20 (see FIG. 4 (B)).

Next, the sample A where a part of the foreign substances are removed by the first positive ion exchange resin 20 is contacted with the negative ion exchange resin 30 and the second positive ion exchange resin 40. The status that the protein contained in the foreign substances in the sample A is adsorbed by the first positive ion exchange resin 20 (area (II) in FIG. 4 (B)) can be explained similar to the status that the protein is adsorbed by the first positive ion exchange resin 20 referring to FIG. 2. Therefore, the detailed description is omitted. The status that the metal salt contained in the foreign substances in the sample A is adsorbed by the negative ion exchange resin 30 and the second positive ion exchange resin 40 (area (III) in FIG. 4 (B)) can be explained similar to the status that the metal salt is adsorbed by the negative ion exchange resin 30 and the second positive ion exchange resin 40 referring to FIG. 3. Therefore, the detailed description is omitted. Either the negative ion exchange resin 30 or the second positive ion exchange resin 40 may be housed as the upper layer thereof, or may be mixed and housed as a lower layer of the first positive ion exchange resin 20.

Finally, after the foreign substances are adsorbed by the ion exchange resin 10, the purified sample A is pooled at the lower layer (see FIG. 4 (C)).

According to the method of purifying nucleic acids according to the second embodiment of the present technology, the foreign substances in the sample A are adsorbed by the first positive ion exchange resin 20 and then are further adsorbed by the negative ion exchange resin 30 and the second positive ion exchange resin 40. Thus, according to the method of purifying nucleic acids according to the second embodiment of the present technology, after the protein having a higher volume is removed, the metal salt having a lower volume can be removed, thereby efficiently removing the foreign substances.

3. A Method of Extracting Nucleic Acids

Next, a method of extracting nucleic acids including the method of purifying nucleic acids according to the respective embodiments will be described. The method of extracting nucleic acids according to the present technology includes the step of ultrasonically treating a sample including nucleic acids, adsorbing substances included in the sample with a positive ion exchange resin and a negative ion exchange resin, and concentrating the nucleic acids by blocking the nucleic acids migrated by electrophoresis as pretreatments for the nuclear acid amplification reaction.

The above-described steps are not especially limited. For example, all steps can be carried out within the same cell. When the respective steps are carried out within the same cell, an ultrasonic generator for an ultrasonic process can be disposed in the cell. In addition, the cell can house the positive ion exchange resin and the negative ion exchange resin. As to the positive ion exchange resin and the negative ion exchange resin, the ion exchange resin 10 (the first positive ion exchange resin 20, the negative ion exchange resin 30 and the second positive ion exchange resin 40) that are used in the method of purifying nucleic acids according to the respective embodiments of the present technology can be used. Also, a negative electrode and a positive electrode for electrophoresis are disposed in the cell, and a blocker for blocking the nucleic acids electrophoresed (e.g., a dialysis membrane, a polymer gel or the like) can be disposed in the cell.

Upon the electrophoresis of the nucleic acids, the intercalator having the anionic functional group can be inserted into the nucleic acids. Examples of the intercalator include a compound having a sulfo functional group. Specific examples include 9,10-anthraquinone-2,6-disulfonic acid, anthraquinone-1-sodium sulfonate, anthraquinone-2,7-disodium sulfonate, anthraquinone-1,5-disodium sulfonate, anthraquinone-2-sodium sulfonate and the like. In this way, when the intercalator having the anionic functional group is inserted into the nucleic acids, an isoelectric point of the nucleic acids can be adjusted in the electrophoresis of the nucleic acids. In other words, the nucleic acids can be concentrated and purified, while an electrophoretic velocity of the nucleic acids is controlled.

Furthermore, carboxyl groups of the protein that is one of the foreign substances included in the sample may be dehydrated and condensed with a compound such as N-hydroxy succin imide (NHS), ethanol amine, ethylene diamine or the like. In the dehydration and condensation reaction, a carbodiimide-based compound can be used as a condensation agent. Specific examples of the carbodiimide-based compound include 1-ethyl-3-(3-dimethylaminopropyl)carbodiimide hydrochloride (EDC), 4,6-dimethoxy-1,3,5-triazin-2-yl)-4-methylmorpholinium chloride (DMT-MM), dicyclohexylcarbodiimide (DCC), diisopropylcarbodiimide (DIC) or the like. Thus, even if the protein is present in the sample upon the electrophoresis of the nucleic acids, a difference between the isoelectric point of the nucleic acids that are dehydrated and condensed with the carboxyl groups in the protein and that of the protein is enlarged, thereby separating the nucleic acid from the protein with high accuracy.

By carrying out the above-described respective steps, the nucleic acids concentrated can be recovered very simply and with high efficiency. In particularly, when the respective steps are carried out within the same cell, an infectious risk to an operator can be reduced when an infectious specimen is handled as the sample, because a transfer of the sample to the other apparatuses is not necessary.

The present technology may have the following configurations.

(1) A method of purifying nucleic acids, including the step of:

adsorbing substances in a sample containing nucleic acids with an ion exchange resin including a positive ion exchange resin and a negative ion exchange resin.

(2) The method of purifying nucleic acids according to (1) above, in which the positive ion exchange resin includes a first positive ion exchange resin and a second positive ion exchange resin having an exclusion limit molecular weight lower than that of the first positive ion exchange resin.

(3) The method of purifying nucleic acids according to (2) above, in which the substances are adsorbed by the first positive ion exchange resin and then are further adsorbed by the negative ion exchange resin and the second positive ion exchange resin.

(4) The method of purifying nucleic acids according to (2) or (3) above, in which the sample is flowed into a column including the first positive ion exchange resin in an upper layer and the negative ion exchange resin and the second positive ion exchange resin in a lower layer from an upper layer side.

(5) The method of purifying nucleic acids according to any one of (1) to (4) above, in which the step is for adsorbing the substances included in the sample that is diluted with a buffer solution by the ion exchange resin, and the buffer solution has a pH of 4.0 to 8.0.

(6) The method of purifying nucleic acids according to any one of (1) to (5) above, in which the positive ion exchange resin is a strong acidic positive ion exchange resin.

(7) The method of purifying nucleic acids according to any one of (2) to (6) above, in which a counter ion of the first positive ion exchange resin is $Na^+$.

(8) The method of purifying nucleic acids according to any one of (2) to (7) above, in which a counter ion of the first positive ion exchange resin is $H^+$.

(9) The method of purifying nucleic acids according to any one of (1) to (8) above, in which the negative ion exchange resin is a strong basic negative ion exchange resin.

(10) The method of purifying nucleic acids according to any one of (1) to (9) above, in which a counter ions of the negative ion exchange resin is $OH^-$.

(11) The method of purifying nucleic acids according to any one of (2) to (10) above, in which a percentage of an ion exchange capacity of the negative ion exchange resin to the second positive ion exchange resin is 50% to 150%.

(12) The method of purifying nucleic acids according to any one of (1) to (11) above, in which a nonionic surfactant and/or a nonionic hydrophilic polymer compound is used to adsorb the substances.

(13) The method of purifying nucleic acids according to any one of (1) to (12) above, in which the substances are foreign substances containing at least a protein and a metal salt.

(14) A method of extracting nucleic acids, including the steps of:
ultrasonically treating the sample including nucleic acids,
adsorbing substances included in the sample with a positive ion exchange resin and a negative ion exchange resin, and
concentrating the nucleic acids by blocking the nucleic acids migrated by electrophoresis.

(15) The method of extracting nucleic acids according to (14) above, in which
the electrophoresis is carried out on the nucleic acids into which an intercalator having an anionic functional group is inserted.

(16) The method of extracting nucleic acids according to (14) or (15) above, in which
the electrophoresis is carried out on the nucleic acids by mixing the sample, a compound having a functional group that is reacted with a carboxyl group of the substances included in the sample by dehydration condensation, and a condensation agent of the dehydration condensation reaction.

(17) A kit for purifying nucleic acids including a positive ion exchange resin; a negative ion resin; and a nucleic acid purifying instrument internally holding the positive ion exchange resin and the negative ion exchange resin for distributing a sample including nucleic acids.

EXAMPLES

1. Effect of Adsorption Treatment by Strong Acidic Positive Ion Exchange Resin on Purifying Ability of Nucleic Acids Test Example 1

100 mg of a strong acidic positive ion exchange resin (Nuvia S Na$^+$ type (manufactured by Bio-Rad Laboratories, Inc.)) was weighed and charged into a spin filter column (Ultrafree-MC, 0.45 µm, manufactured by Millipore). Next, 50 mM MES buffer (pH of 5) (manufactured by Dojindo Molecular Technologies, Inc.) was prepared. To the buffer, 0.5% by mass of BSA (manufactured by Wako Pure Chemical Industries, Ltd.) was added and then 5 µM of Cy3-modified 20 mer oligoDNAs (manufactured by Sigma Aldrich Co.) was added. After a blended liquid of the protein and the nucleic acids was sufficiently agitated at normal temperature, 200 µL of the blended liquid was dropped into a spin column filled with the strong acidic positive ion exchange resin and was sufficiently agitated. Thereafter, the blended liquid was centrifuged and spun down at 12000 G for 2 minutes. The spun-down liquid was measured for absorbance using NanoDrop D-1000 (manufactured by Thermo Fisher Scientific Inc.). From a difference between the absorbances before and after the treatment by the strong acidic positive ion exchange resin, a purifying ability of nucleic acids was evaluated. The absorbance of the BSA was evaluated in a protein A280 mode whereas the absorbance of the nucleic acids was evaluated as the absorbance of Cy3 in a micro array mode. Furthermore, in order to close to a biological environment, to the protein-nucleic acid blended liquid, 0.09% by mass (at a final concentration) of NaCl (manufactured by Wako Pure Chemical Industries, Ltd.) was added. Similarly, the treatment was carried out by the strong acidic positive ion exchange resin.

Figure 5:
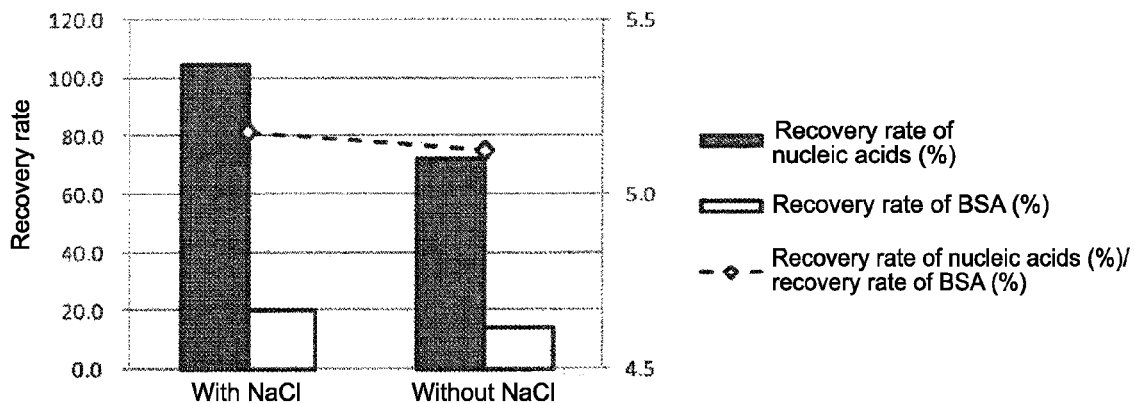
FIG. 5 A graph showing recovery rates of nucleic acids after an adsorption treatment by the positive ion exchange resin (Test Example 1).

Results of the evaluation are shown in FIG. 5. As shown in FIG. 5, from the concentration of the Cy3 oligoDNAs and the BSA before and after the treatment by the strong acidic positive ion exchange resin, the recovery rate of the nucleic acids including NaCl was about 100%, and the recovery rate of the nucleic acids including no NaCl was about 72%. On the other hand, the recovery rate of the BSA including NaCl was about 20%, and the recovery rate of the BSA including no NaCl was about 14%. From these facts, it revealed that, by carrying out the treatment by the strong acidic positive ion exchange resin, a DNA presence ratio can be increased in a blended system of the protein and the nucleic acids.

Figure 6:
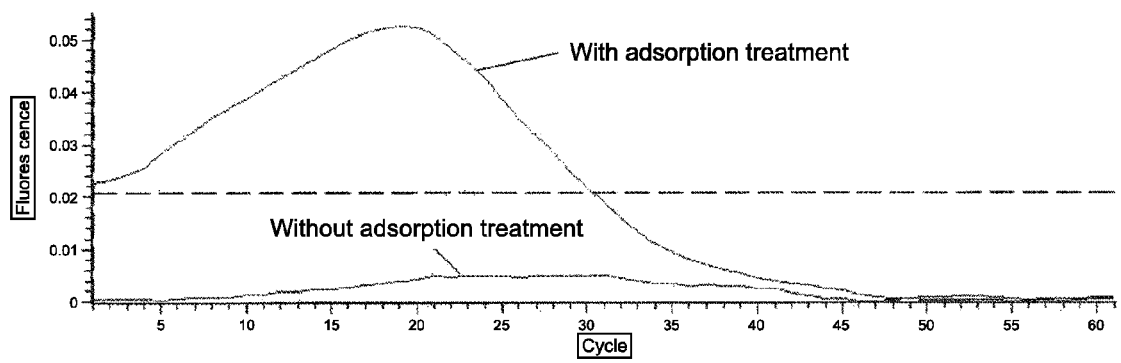
FIG. 6 A graph showing a result of a LAMP reaction of a sample after an adsorption treatment by the positive ion exchange resin (Test Example 1).

FIG. 6 shows a result of a LAMP reaction of a sample after an adsorption treatment of foreign substances by the positive ion exchange resin and a sample without the adsorption treatment. A LAMP reaction liquid was prepared by blending the sample, an enzyme, a fluorescent pigment, a nucleic acid monomer, a buffer, a primer set for a target nucleic acid chain amplification and a probe for real-time measurements. Each concentration was determined by a Loopamp DNA amplification kit (manufactured by Eiken Chemical Co., Ltd.) and a Loopamp RNA amplification kit (manufactured by Eiken Chemical Co., Ltd.). The reaction temperature was at 63° C. The LAMP reaction was measured by making use of a thermal cycler Chromo4 (manufactured by Bio Rad, US) capable of carrying out real-time measurements. 1 cycle was set to 1 min. The used probe was a QP probe which was a quenching probe so that the amplification of the nucleic acids and the decrease of the fluorescence intensity can be observed. For more information on the QP probe which is J-bio21, refer to a Japanese website, http://www.j-bio21.co.jp/tech/qpmethod.htm dated Jul. 19, 2011 with a title of "QP Method." As shown in FIG. 6, the nuclear acid amplification reaction was detected on the sample after the adsorption treatment of the foreign substances by the ion exchange resin. The LAMP reaction as described later was carried out as described above.

2. Review about Counter Ion of Positive Ion Exchange Resin

Test Sample 2

Figure 7:
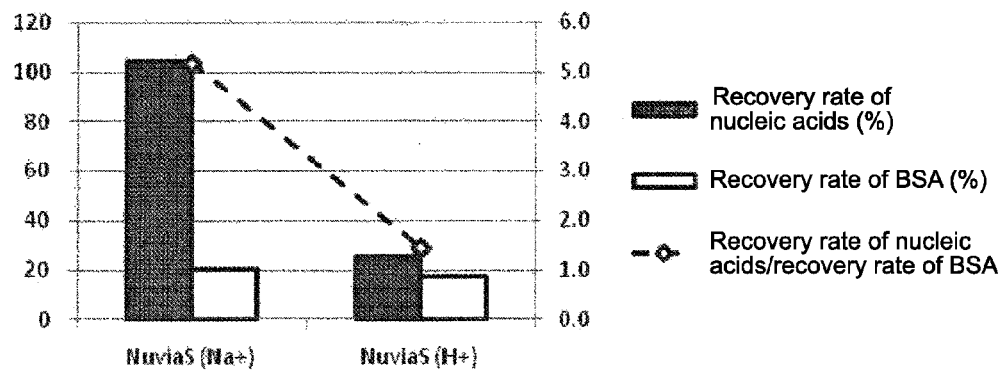
FIG. 7 A graph showing a result of reviewing an effect of the positive ion exchange resin on recovery rates of counter ion species ($Na^+$, $H^+$) (Test Example 2).

100 mg of a positive ion exchange resin (Nuvia S Na$^+$ type (manufactured by Bio-Rad Laboratories, Inc.)) was weighed and charged into a spin filter column (Ultrafree-MC, 0.45 µm). The above-described positive ion exchange resin (Nuvia S Na$^+$ type) was flowed through a 1M HCl solution and was cleaned with pure water to be neutral to prepare a positive ion exchange resin (Nuvia S H$^+$ type). 100 mg of the positive ion exchange resin (Nuvia S H$^+$ type) was weighed and charged into the spin filter column (Ultrafree-MC, 0.45 µm). Next, 50 mM MES buffer (pH of 5) was prepared. To the buffer, 0.5% by mass of BSA was added and then 4 µM of Cy3-modified 20 mer oligoDNAs was added. In addition, 0.09% by mass of NaCl was added. After each sample was sufficiently agitated at normal temperature, 200 µL of each sample was dropped into a spin column filled with a Na$^+$ type strong acidic positive ion exchange resin or a H$^+$ type strong acidic positive ion exchange resin and was sufficiently agitated. Thereafter, the blended liquid was centrifuged and spun down at 12000 G for 2 minutes. The purifying ability of nucleic acids by each strong acidic positive ion exchange resin was evaluated similar to the text example 1. The concentration of Na$^+$ was measured using Horiba Cardy Sodium Compact Ion Meter (C-122) (manufactured by HORIBA Ltd.) The pH was measured using a pocket pH meter S2K712 (manufactured by ISFETCOM Co., Ltd.). Results of the evaluation are shown in FIG. 7. A summary of the evaluation results are shown in Table 1.

TABLE 1

|  | Before adsorption | Na+ type | H+ type |
|---|---|---|---|
| Recovery rate of nucleic acids (%) | 100 | 100 | 26 |
| Recovery rate of BSA (%) | 100 | 20 | 18 |
| Recovery rate of nucleic acids/recovery rate of BSA | 1.0 | 5.2 | 1.5 |
| Na+ concentration (ppm) | 450 | 450 | 46 |
| pH | 4.9 | 5.2 | 2.2 |

It revealed that the recovery rate of the nucleic acids and the purifying rate were higher when the Na+ type strong acidic positive ion exchange resin was used than those when the H+ type strong acidic positive ion exchange resin. On the other hand, the concentration of was higher and demineralization less occurred when the Na+ type strong acidic positive ion exchange resin was used as compared with when the H+ type strong acidic positive ion exchange resin was used.

It revealed that the pH of the sample after the adsorption treatment was lower than the pH of the sample before the adsorption treatment when the H+ type strong acidic positive ion exchange resin was used as compared with when the Na+ type strong acidic positive ion exchange resin was used. This may because negative charges of the nucleic acids were weakened, the nucleic acids were easily held non-specifically on the H+ of the strong acidic positive ion exchange resin and the recovery rate of the nucleic acid was decreased when the H+ type strong acidic positive ion exchange resin was used as compared with when the Na+ type strong acidic positive ion exchange resin was used.

3. Review about Salt Concentration

Test Example 3

This Test Example reviews an effect of a salt concentration in a sample when the positive ion exchange resin adsorbs the foreign substance in the sample.

100 mg of a positive ion exchange resin (Nuvia S Na+ type (manufactured by Bio-Rad Laboratories, Inc.)) was weighed and charged into a spin filter column (Ultrafree-MC, 0.45 μm). Next, 50 mM MES buffer (pH of 5) was prepared. To the buffer, 0.5% by mass of BSA was added, then 4 μM of Cy3-modified 20 mer oligoDNAs was added, and further 3.3, 0.9 or 0.33 mg/mL of NaCl was added to prepare three samples. Another sample was prepared under the condition similar to the above-described three samples except that no NaCl was added. After each samples was sufficiently agitated at normal temperature, 200 μL of each sample was dropped into a spin column filled with a Na+ type strong acidic positive ion exchange resin or a H+ type strong acidic positive ion exchange resin and was sufficiently agitated. Thereafter, the blended liquid was centrifuged and spun down at 12000 G for 2 minutes. The purifying ability of nucleic acids by each strong acidic positive ion exchange resin was evaluated similar to the text examples 1 and 2. A summary of evaluation results are shown in Table 2.

TABLE 2

|  | NaCl concentration (mg/mL) | | | |
|---|---|---|---|---|
|  | 3.3 | 0.9 | 0.33 | 0 |
| Recovery rate of nucleic acids (%) | 99 | 100 | 100 | 79 |
| Recovery rate of BSA (%) | 20 | 20 | 20 | 17 |
| Recovery rate of nucleic acids (%)/recovery rate of BSA (%) | 5.0 | 5.2 | 4.9 | 4.6 |

It revealed that the recovery rate of the nucleic acids was higher when the NaCl concentration was 0.33, 0.9 or 3.3 mg/ml as compared with when the concentration was 0 mg/mL. The recovery rate of the nucleic acids was 100% when the NaCl concentration was 0.33, 0.9 or 3.3 mg/ml. Based on the results, when the sample including the salt such as blood is used to carry out the nucleic acid purification, addition of the salt to the sample upon purification may not be necessary. On the other hand, when the sample including no salt such as bacteria is used to carry out the nucleic acid purification, addition of the salt to the sample upon purification may be desirable.

4. Effect of Ion Exchange Resin Species on Demineralization

Hereinbelow, an effect of ion exchange resin species on demineralization was reviewed in Examples 1 to 3 and Comparative Examples 1 and 2.

Example 1

100 mg of a strong acidic positive ion exchange resin (Nuvia S (Na+ type) (manufactured by Bio-Rad Laboratories, Inc.)), 50 mg of a strong acidic positive ion exchange resin (AG1-X8 (H+ type) (manufactured by Bio-Rad Laboratories, Inc.)) and 50 mg of a strong basic negative ion exchange resin (AG50W-X8 (OH− type) (manufactured by Bio-Rad Laboratories, Inc.)) were weighed and charged into a spin filter column (Ultrafree-MC, 0.45 μm). Before the adsorption treatment, the concentration of Na+ was 0.45 mg/mL and the pH was 4.9. Next, 50 mM MES buffer (pH of 5) was prepared. To the buffer, bovine whole blood was added to dilute to 1/10 times, thereby preparing a sample. After the sample was sufficiently agitated at normal temperature, 200 μL of the sample was dropped into a spin column filled with the above-described ion exchange resin and was sufficiently agitated. Thereafter, the blended liquid was centrifuged and spun down at 12000 G for 2 minutes. The concentration of Na+ and the pH of the sample were measured.

Example 2

50 mg of a strong acidic positive ion exchange resin (AG1-X8 (H+ type) (manufactured by Bio-Rad Laboratories, Inc.)) and 50 mg of a strong basic negative ion exchange resin (AG50W-X8 (OH− type) (manufactured by Bio-Rad Laboratories, Inc.)) were used instead of 100 g of the strong acidic positive ion exchange resin (Nuvia S (Na+ type) (manufactured by Bio-Rad Laboratories, Inc.)), 50 mg of the strong acidic positive ion exchange resin (AG1-X8 (H+ type) (manufactured by Bio-Rad Laboratories, Inc.))

and 50 mg of the strong basic negative ion exchange resin (AG50W-X8 (OH⁻ type) (manufactured by Bio-Rad Laboratories, Inc.)) in Example 1 and were evaluated similar to Example 1.

Example 3

70 mg of a strong acidic positive ion exchange resin (AG1-X8 (H⁺ type) (manufactured by Bio-Rad Laboratories, Inc.)) and 50 mg of a strong basic negative ion exchange resin (AG50W-X8 (OH⁻ type) (manufactured by Bio-Rad Laboratories, Inc.)) were used instead of 50 g of the strong acidic positive ion exchange resin (AG1-X8 (H⁺ type) (manufactured by Bio-Rad Laboratories, Inc.)) and 50 mg of the strong basic negative ion exchange resin (AG50W-X8 (OH⁻ type) (manufactured by Bio-Rad Laboratories, Inc.)) in Example 2 and were evaluated similar to Example 2.

Comparative Example 1

Only 100 mg of a strong acidic positive ion exchange resin (Nuvia S (Na⁺ type) (manufactured by Bio-Rad Laboratories, Inc.)) was used instead of 100 mg of the strong acidic positive ion exchange resin (Nuvia S (Na⁺ type) (manufactured by Bio-Rad Laboratories, Inc.)), 50 mg of the strong acidic positive ion exchange resin (AG1-X8 (H⁺ type) (manufactured by Bio-Rad Laboratories, Inc.)) and 50 mg of the strong basic negative ion exchange resin (AG50W-X8 (OH⁻ type) (manufactured by Bio-Rad Laboratories, Inc.)) in Example 1 and was evaluated similar to Example 1.

Comparative Example 2

Only 50 mg of a strong acidic positive ion exchange resin (AG1-X8 (H⁺ type) (manufactured by Bio-Rad Laboratories, Inc.)) was used instead of 100 mg of the strong acidic positive ion exchange resin (Nuvia S (Na⁺ type) (manufactured by Bio-Rad Laboratories, Inc.)), 50 mg of the strong acidic positive ion exchange resin (AG1-X8 (H⁺ type) (manufactured by Bio-Rad Laboratories, Inc.)) and 50 mg of the strong basic negative ion exchange resin (AG50W-X8 (OH⁻ type) (manufactured by Bio-Rad Laboratories, Inc.)) in Example 1 and was evaluated similar to Example 1.

A summary of the evaluation results in Examples 1 to 3 and Comparative Examples 1 and 2 are shown in Table 3.

in the pH in the sample was inhibited with higher accuracy as compared with Comparative Example 2.

As shown in Example 2 and Example 3, it suggested that a demineralization effect was provided and the variation in the pH was inhibited even when the amount of the strong acidic positive ion exchange resin and the amount of the strong basic negative ion exchange resin were the same.

5. Effect of Demineralization on LAMP Reaction and RT-LAMP Reaction

Hereinbelow, an effect of demineralization on a LAMP reaction and a RT-LAMP reaction was reviewed in Examples 4 and 5 and Comparative Examples 3 to 5.

Example 4

100 mg of a positive ion exchange resin (Nuvia S Na⁺ type (manufactured by Bio-Rad Laboratories, Inc.)), 50 mg of a strong acidic positive ion exchange resin (Nuvia S (Na⁺ type) (manufactured by Bio-Rad Laboratories, Inc.)) and 50 mg of a strong basic negative ion exchange resin (AG50W-X8 (OH⁻ type) (manufactured by Bio-Rad Laboratories, Inc.)) were weighed and charged into a spin filter column (Ultrafree-MC, 0.45 µm). Next, 50 mM MES buffer (pH of 5) was prepared. To the buffer, 1000 copy/µL of bifidobacteria ultrasonically disintegrated was added, then 0.9 mg/mL of NaCl was added. After a sample obtained was sufficiently agitated at normal temperature, 200 µL of each sample was dropped into a spin column filled with a Na⁺ type or a H⁺ type strong acidic positive ion exchange resin and was sufficiently agitated. Thereafter, the blended liquid was centrifuged and spun down at 12000 G for 2 minutes. The LAMP reaction and the RT-LAMP reaction were measured to similar to the text example 1.

Example 5

50 mg of a strong acidic positive ion exchange resin (AG1-X8 (H⁺ type) (manufactured by Bio-Rad Laboratories, Inc.)) and 50 mg of a strong basic negative ion exchange resin (AG50W-X8 (OH⁻ type) (manufactured by Bio-Rad Laboratories, Inc.)) were used instead of 100 g of the strong acidic positive ion exchange resin (Nuvia S (Na⁺

TABLE 3

|  | Before adsorption treatment | After adsorption treatment | | | | |
| --- | --- | --- | --- | --- | --- | --- |
|  | — | Example 1 | Example 2 | Example 3 | Comparative Example 1 | Comparative Example 2 |
| Ion exchange resin | — | Nuvia S + AG mix | AG mix | AG mix | Nuvia S | AG1-X8 (H⁺) |
| Na⁺ | 0.45 | 0.002 | 0.004 | 0.006 | 0.45 | 0.017 |
| pH | 4.9 | 5.5 | 5.2 | 5.6 | 5.2 | 1.9 |

In each Example 1, Example 2 and Example 3, the ion exchange resin including the H⁺ type strong acidic positive ion exchange resin and the OH⁻ type strong basic negative ion exchange resin was used, whereby each sample was demineralized with higher accuracy as compared with those in Comparative Example 1 and Comparative Example 2. Also, in Example 1, Example 2 and Example 3, the variation type) (manufactured by Bio-Rad Laboratories, Inc.)), 100 g of the strong acidic positive ion exchange resin (AG1-X8 (H⁺ type) (manufactured by Bio-Rad Laboratories, Inc.)) and 50 mg of the strong basic negative ion exchange resin (AG50W-X8 (OH⁻ type) (manufactured by Bio-Rad Laboratories, Inc.)) in Example 4 and were evaluated similar to Example 4.

Comparative Example 3

A sample to which no NaCl was added was used and the sample was not dropped into the spin column filled with the ion exchange resin dissimilar to Example 4, but was evaluated similar to Example 4.

Comparative Example 4

A sample was not dropped into the spin column filled with the ion exchange resin dissimilar to Example 4, but was evaluated similar to Example 4.

Comparative Example 5

100 mg of a strong acidic positive ion exchange resin (Nuvia S ($Na^+$ type) (manufactured by Bio-Rad Laboratories, Inc.)) was used instead of 100 g of the strong acidic positive ion exchange resin (Nuvia S ($Na^+$ type) (manufactured by Bio-Rad Laboratories, Inc.)), 50 mg of the strong acidic positive ion exchange resin (AG1-X8 ($H^+$ type) (manufactured by Bio-Rad Laboratories, Inc.)) and 50 mg of the strong basic negative ion exchange resin (AG50W-X8 ($OH^-$ type) (manufactured by Bio-Rad Laboratories, Inc.)) in Example 4 and were evaluated similar to Example 4.

Figure 8:
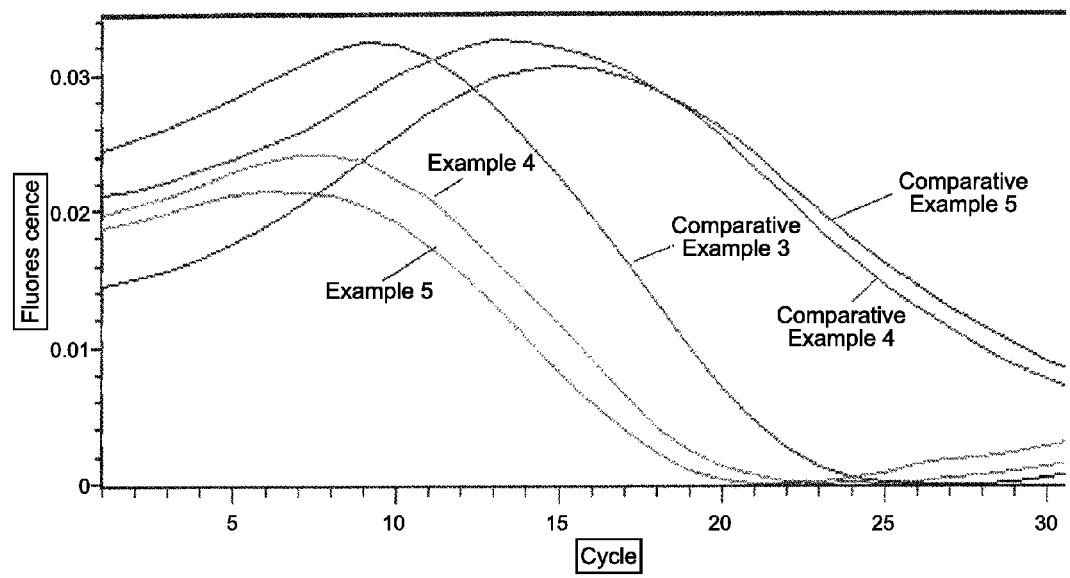
FIG. 8 A graph showing a result of the LAMP reaction of the sample after an adsorption treatment by the ion exchange resin (Examples 4 and 5).
Figure 9:
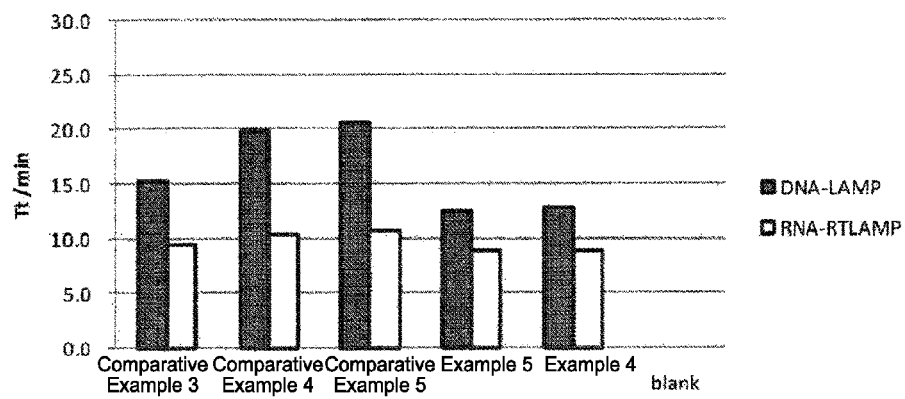
FIG. 9 A graph showing a result of the LAMP reaction and an RT-LAMP reaction (a Tf value) of the sample after an adsorption treatment by the positive ion exchange resin (Examples 4 and 5).

A summary of the evaluation results in Examples 4 and 5 and Comparative Examples 3 to 5 are shown in FIG. 8 and FIG. 9. Example 4, Example 5 and Comparative Example 4 revealed that when the sample was demineralized by the ion exchange resin, Tt values of the LAMP reaction and the RT-LAMP reaction were decreased. Example 4, Example 5 and Comparative Example 4 suggest that when the sample is demineralized by the ion exchange resin, the LAMP reaction can proceed successfully. Example 4 and Example 5 revealed that an effect of using the strong acidic positive ion exchange resin (Nuvia S $Na^+$ type (manufactured by Bio-Rad Laboratories, Inc.)) as the ion exchange resin on the LAMP reaction was small. It is contemplated that an effect of using the strong acidic positive ion exchange resin (Nuvia S $Na^+$ type (manufactured by Bio-Rad Laboratories, Inc.)) as the ion exchange resin on the demineralization of the sample is small. In addition, the LAMP reaction proceeded unsuccessfully in Comparative Example 4 and Comparative Example 5. This suggests that the sample is sufficiently demineralized in order to proceed the LAMP reaction successfully.

6. Review about Additives

Hereinbelow, an effect of additives (Brij35 and EDTA) was reviewed in Example 6 and Example 7.

Example 6

100 mg of a strong acidic positive ion exchange resin (Nuvia S ($Na^+$ type) (manufactured by Bio-Rad Laboratories, Inc.)), 50 mg of a strong acidic positive ion exchange resin (AG1-X8 ($H^+$ type) (manufactured by Bio-Rad Laboratories, Inc.)) and 50 mg of a strong basic negative ion exchange resin (AG50W-X8 ($OH^-$ type) (manufactured by Bio-Rad Laboratories, Inc.)) were weighed and charged into a spin filter column (Ultrafree-MC, 0.45 μm). Next, 50 mM MES buffer (pH of 5) was prepared. To the buffer, 10% by volume of bovine whole blood was added, 1000 copy/μL of bifidobacteria ultrasonically disintegrated was added, 0.5% by volume of Briji35 was added, and 1 mL of EDTA was added. The LAMP reaction and the RT-LAMP reaction were carried out and evaluated on the resultant sample containing nucleic acids similar to Example 4.

Example 7

A Brij35 and EDTA were not added to the sample dissimilar to Example 6, but the sample was evaluated similar to Example 6.

Figure 10:
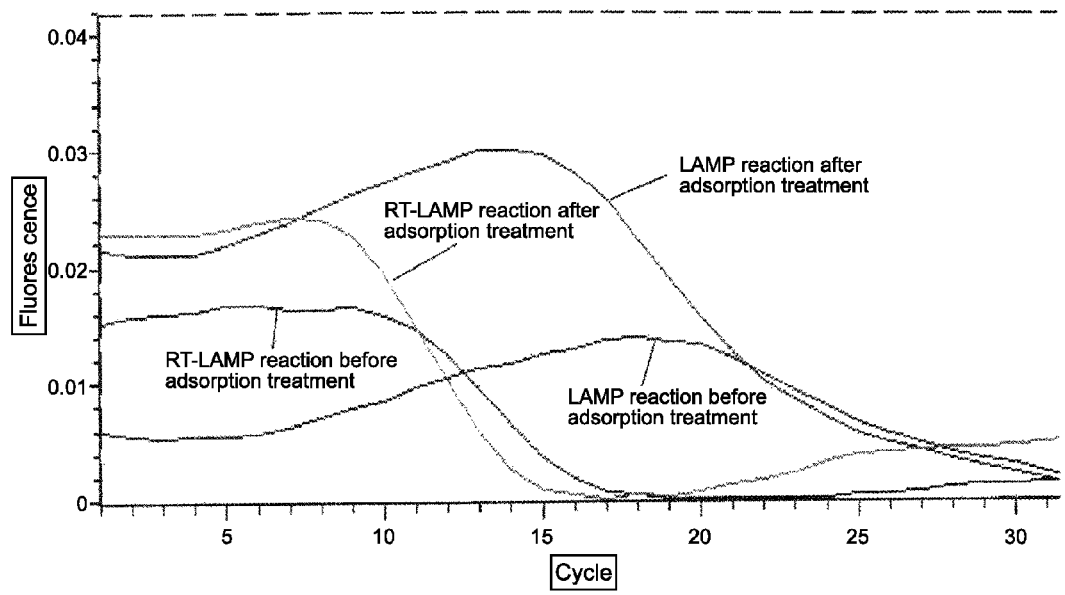
FIG. 10 A graph showing a result of the LAMP reaction and the RT-LAMP reaction (a Tt value) after an adsorption treatment by the positive ion exchange resin (Example 6).
Figure 11:
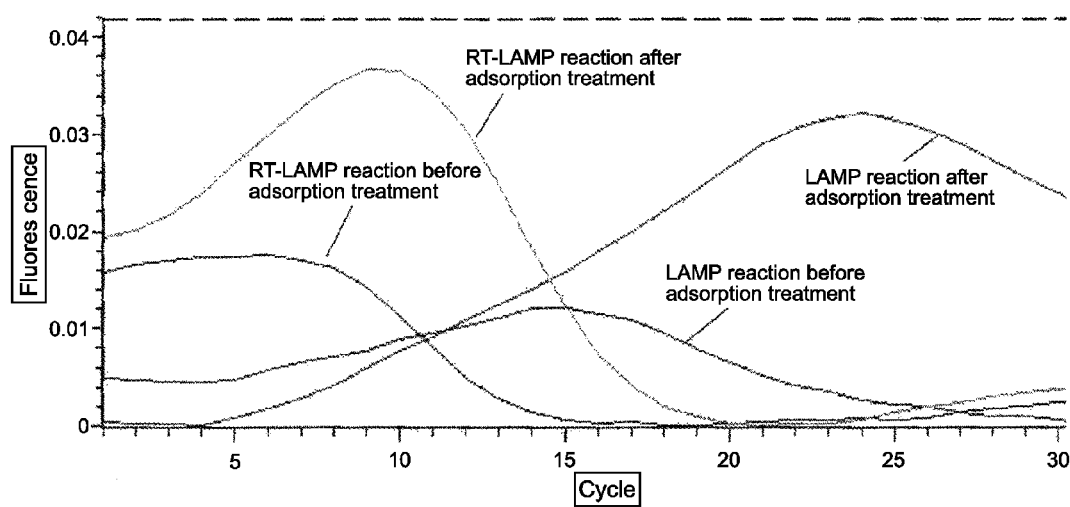
FIG. 11 A graph showing a result of the LAMP reaction and the RT-LAMP reaction (a Tt value) after an adsorption treatment by the ion exchange resin (Example 7).

Results of the evaluation in Example 6 and Example 7 are shown in FIGS. 10 and 11. A summary of the evaluation results are shown in Table 4.

TABLE 4

|  | Example 6 | | Example 7 | |
| --- | --- | --- | --- | --- |
|  | LAMP Tt (min) | RT-LAMP Tt (min) | LAMP Tt (min) | RT-LAMP Tt (min) |
| Before adsorption treatment | 23.0 | 12.4 | 19.2 | 9.9 |
| After adsorption treatment | 19.3 | 10.8 | 28.8 | 12.8 |

In Example 6, it revealed that when the foreign substances in the sample were adsorbed by the ion exchange resin, the Tt values in both of the LAMP reaction and the RT-LAMP reaction were decreased as compared with those before the adsorption treatment. On the other hand, in Example 7, it revealed that when the foreign substances in the sample were adsorbed by the ion exchange resin, the Tt values in both of the LAMP reaction and the RT-LAMP reaction were increased as compared with those before the adsorption treatment. This may because the recovery rate of the nucleic acids was increased by adding Briji 35 and 1 mL of EDTA to the sample in Example 6 dissimilar to Example 7.

7. Review about Surfactant/Hydrophilic Polymer

Hereinbelow, an effect of a surfactant/a hydrophilic polymer was reviewed in Examples 8 to 11.

Example 8

100 mg of a strong acidic positive ion exchange resin (Nuvia S ($Na^+$ type) (manufactured by Bio-Rad Laboratories, Inc.)), 50 mg of a strong acidic positive ion exchange resin (AG1-X8 ($H^+$ type) (manufactured by Bio-Rad Laboratories, Inc.)) and 50 mg of a strong basic negative ion exchange resin (AG50W-X8 ($OH^-$ type) (manufactured by Bio-Rad Laboratories, Inc.)) were weighed and charged into a spin filter column (Ultrafree-MC, 0.45 μm). Next, 50 mM MES buffer (pH of 5) was prepared. To the buffer, 10% by volume of bovine whole blood was added, 1000 copy/μL of bifidobacteria ultrasonically disintegrated was added, and 0.5% by volume of Briji35 was further added. In Example 7, a nonionic surfactant or a nonionic hydrophilic polymer was not added to the sample. The recovery rate of the nucleic acids was evaluated on the resultant sample containing nucleic acids similar to Test Example 1.

Example 9

0.5% by volume of Brij35 was added as the nonionic surfactant to the sample before the adsorption treatment by the ion exchange resin dissimilar to Example 8, but the sample was evaluated similar to Example 8.

Example 10

Tween 20 was used instead of Brij35 as the nonionic surfactant dissimilar to Example 9, but the sample was evaluated similar to Example 9.

Example 11

PEG20000 was used instead of Brij35 as the nonionic surfactant dissimilar to Example 9, but the sample was evaluated similar to Example 9.

Results of the evaluation in Examples 8 to 11 are shown in Table 5.

TABLE 5

|  | Example 8 | Example 9 | Example 10 | Example 11 |
|---|---|---|---|---|
| Recovery rate of nucleic acids (%) | 56 | 78 | 77 | 62 |

The recovery rates of the nucleic acids in Examples 8 to 10 were higher than that in Example 7. It exemplified that the recovery rate of the nucleic acids was increased by adding the non-ionic surfactant (Brij35, Tween20) or the nonionic hydrophilic polymer (PEG20000) to the sample to carry out the adsorption treatment of the sample.

8. Comparison of Adsorption Treatment According to Present Technology with Adsorption Treatment by Zeolite Example 12 and Comparative Example 6 were carried out to compare the adsorption treatment according to the present technology and the adsorption treatment by zeolite.

Example 12

A sample was prepared similar to Example 7. The LAMP reaction and the RT-LAMP reaction were carried out and evaluated three times on three samples each having the same composition similar to Example 7.

Comparative Example 6

50 mM MES buffer (pH of 5) was prepared. To the buffer, 5% by volume of bovine whole blood was added, and 1000 copy/μL of bifidobacteria ultrasonically disintegrated was added to prepare a sample. Next, an alkali and heat treatment was carried out on the sample, and the foreign substances were adsorbed by zeolite. The LAMP reaction and the RT-LAMP reaction were carried out and evaluated three times on three samples each having the same composition similar to Example 4.

Figure 12:
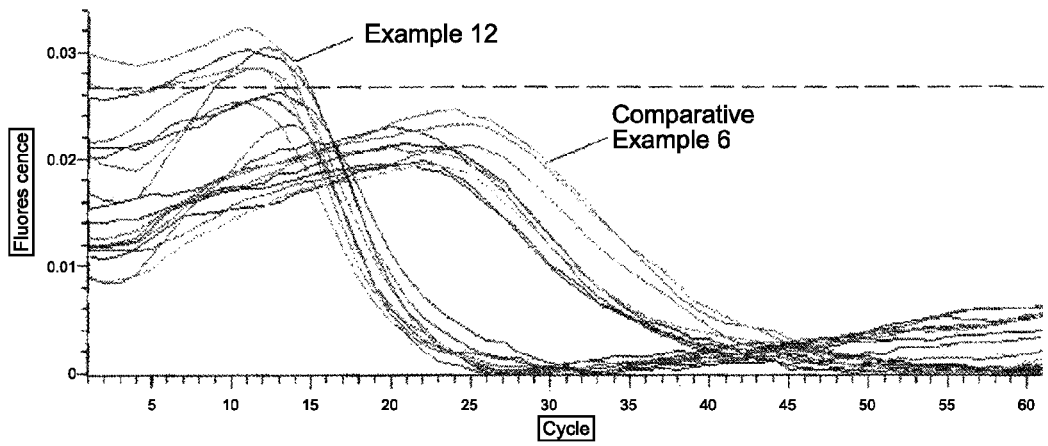
FIG. 12 A graph showing a result of the LAMP reaction of the sample (Example 12).
Figure 13:
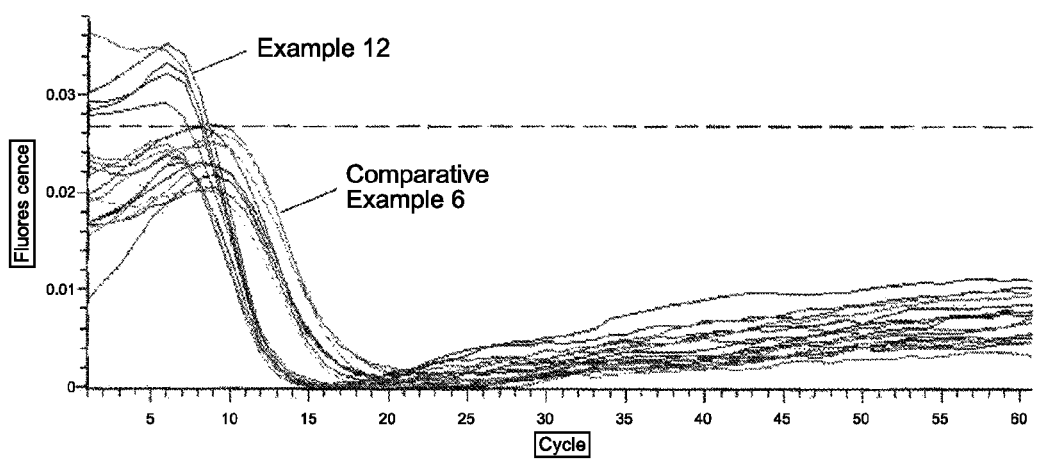
FIG. 13 A graph showing a result of the RT-LAMP reaction of the sample (Example 12).

Results of the evaluation in Example 12 and Comparative Example 6 are shown in FIG. 12 (the LAMP reaction) and in FIG. 13 (the RT-LAMP reaction). Example 12 and Comparative Example 6 revealed that the nuclear acid amplification reaction proceeded more successfully when the foreign substances in the sample were adsorbed by the ion exchange resin as compared when the foreign substances in the sample were adsorbed by the zeolite.

INDUSTRIAL APPLICABILITY

According to the method of purifying nucleic acids according to the present technology, the operation is simple and the nucleic acids can be extracted in a short time with high efficiency. Accordingly, the method can be applied to a nucleic acid purifying treatment for the nuclear acid amplification reaction such as PCR (Polymerase Chain Reaction) and LAMP (Loop-Mediated Isothermal Amplification) and can be used to purify only a minor amount or an extremely low concentration of the nucleic acids included in the sample.

DESCRIPTION OF REFERENCE NUMERALS

1, 101 kit for purifying nucleic acids
3 nucleic acid purifying instrument
10 ion exchange resin
20 first positive ion exchange resin
30 negative ion exchange resin
40 second positive ion exchange resin

The invention claimed is:

1. A method of purifying nucleic acids comprising the step of:
adsorbing substances in a sample containing nucleic acids with an ion exchange resin including a positive ion exchange resin and a negative ion exchange resin, wherein
the positive ion exchange resin includes a first positive ion exchange resin and a second positive ion exchange resin having an exclusion limit molecular weight lower than that of the first positive ion exchange resin.

2. The method of purifying nucleic acids according to claim 1, wherein the substances are adsorbed by the first positive ion exchange resin and then are further adsorbed by the negative ion exchange resin and the second positive ion exchange resin.

3. The method of purifying nucleic acids according to claim 2, wherein
the sample is flowed into a column including the first positive ion exchange resin in an upper layer and the negative ion exchange resin and the second positive ion exchange resin in a lower layer from an upper layer side.

4. The method of purifying nucleic acids according to claim 3, wherein
the step is for adsorbing the substances included in the sample that is diluted with a buffer solution by the ion exchange resin, and the buffer solution has a pH of 4.0 to 8.0.

5. The method of purifying nucleic acids according to claim 4, wherein the positive ion exchange resin is a strong acidic positive ion exchange resin.

6. The method of purifying nucleic acids according to claim 5, wherein a counter ion of the first positive ion exchange resin is $Na^+$.

7. The method of purifying nucleic acids according to claim 6, wherein a counter ion of the second positive ion exchange resin is $H^+$.

8. The method of purifying nucleic acids according to claim 7, wherein the negative ion exchange resin is a strong basic negative ion exchange resin.

9. The method of purifying nucleic acids according to claim 8, wherein a counter ion of the negative ion exchange resin is $OH^-$.

10. The method of purifying nucleic acids according to claim 9, wherein
a percentage of an ion exchange capacity of the negative ion exchange resin to the second positive ion exchange resin is 50% to 150%.

11. The method of purifying nucleic acids according to claim 10, wherein
a nonionic surfactant and/or a nonionic hydrophilic polymer compound is used to adsorb the substances.

12. The method of purifying nucleic acids according to claim 11, wherein the substances are foreign substances containing at least a protein and a metal salt.

13. A method of extracting nucleic acids, comprising the steps of:
ultrasonically treating the sample including nucleic acids,
adsorbing substances included in the sample with a positive ion exchange resin and a negative ion exchange resin, and
concentrating the nucleic acids by blocking the nucleic acids migrated by electrophoresis.

14. The method of extracting nucleic acids according to claim 13, wherein the electrophoresis is carried out on the nucleic acids into which an intercalator having an anionic functional group is inserted.

15. The method of extracting nucleic acids according to claim 14, wherein
the electrophoresis is carried out on the nucleic acids by mixing the sample, a compound having a functional group that is reacted with a carboxyl group of the substances included in the sample by dehydration condensation, and a condensation agent of the dehydration condensation reaction.

16. A kit for purifying nucleic acids comprising:
a positive ion exchange resin;
a negative ion resin; and
a nucleic acid purifying instrument internally holding the positive ion exchange resin and the negative ion exchange resin for distributing a sample including nucleic acids,
wherein the positive ion exchange resin includes a first positive ion exchange resin and a second positive ion exchange resin having an exclusion limit molecular weight lower than that of the first positive ion exchange resin.

17. The kit of claim 16, wherein the positive ion exchange resin is a strong acidic positive ion exchange resin.

18. The kit of claim 17, wherein a counter ion of the first positive ion exchange resin is $Na^+$.

19. The kit of claim 18, wherein a counter ion of the second positive ion exchange resin is $H^+$.

20. The kit of claim 16, wherein a percentage of an ion exchange capacity of the negative ion exchange resin to the second positive ion exchange resin is 50% to 150%.

* * * * *